(12) United States Patent
Wolfson

(10) Patent No.: US 9,265,529 B2
(45) Date of Patent: Feb. 23, 2016

(54) ORTHOPEDIC FIXATION SYSTEMS AND METHODS

(76) Inventor: Nikolaj Wolfson, San Francisco, CA (US)

(*) Notice: Subject to any disclaimer, the term of this patent is extended or adjusted under 35 U.S.C. 154(b) by 0 days.

(21) Appl. No.: 13/308,184

(22) Filed: Nov. 30, 2011

(65) Prior Publication Data

US 2012/0143190 A1    Jun. 7, 2012

Related U.S. Application Data

(63) Continuation-in-part of application No. 12/956,768, filed on Nov. 30, 2010.

(51) Int. Cl.
*A61B 17/60* (2006.01)
*A61B 17/64* (2006.01)
*A61B 17/62* (2006.01)

(52) U.S. Cl.
CPC ............... *A61B 17/62* (2013.01); *A61B 17/64* (2013.01)

(58) Field of Classification Search
CPC ...... A61B 17/62; A61B 17/64; A61B 17/645; A61B 17/6466; A61B 17/6458
USPC .............. 606/53–59, 90, 105, 87; 602/32–40
See application file for complete search history.

(56) References Cited

U.S. PATENT DOCUMENTS

| | | | |
|---|---|---|---|
| 661,812 A | 11/1900 | McKown et al. | |
| 2,020,262 A | 11/1935 | Longfellow | |
| 2,032,653 A | 3/1936 | Ettinger | |
| 2,035,952 A | 3/1936 | Ettinger | |
| 2,079,567 A | 5/1937 | Anderson | |
| 2,080,802 A | 5/1937 | Anderson | |
| 2,101,889 A | 12/1937 | Anderson | |
| 2,120,446 A | 6/1938 | Albert | |
| 2,185,322 A | 1/1940 | Anderson | |
| 2,204,266 A | 6/1940 | Wilcox | |
| 2,214,490 A | 9/1940 | Thomas | |
| 2,238,869 A | 4/1941 | Haynes | |
| 2,391,537 A * | 12/1945 | Anderson | 606/59 |
| 2,393,831 A * | 1/1946 | Stader | 606/56 |
| 2,756,082 A * | 7/1956 | Pucci | 403/107 |
| 3,615,087 A * | 10/1971 | Hickman | 69/244 |

(Continued)

OTHER PUBLICATIONS

Pichkhadze, Issak M., MD, PhD, "Pichkhadze's Apparatus for Monopolar, Bipolar and Polypolar Stabilziation and Ability to Assemble (Align) the Bone Fragments in 3D," 2002 [retrieved on May 7, 2010]. Retrieved from the Internet:< URL: http://www.orthopaed-rmp.ru/3_3e.html>.

*Primary Examiner* — Jacqueline Johanas

(57) ABSTRACT

Collapsible orthopedic fixation assemblies and related methods are disclosed. A collapsible fixation assembly includes end frames that are coupled with one or more cross beams. The fixation assembly is reconfigurable between a collapsed configuration in which the end frames are substantially aligned with the one or more cross beams and a deployed configuration in which the end frames are oriented transverse to the one or more cross beams and in which relative movement between the end frames and the one or more cross beams can be inhibited. The fixation assembly is configured to support at least one bone-interface component, which is configured to constrain a bone of a patient. In the collapsed configuration, the fixation assemblies is more compact than in the deployed configuration, thereby making it more easy to store and transport as compared to a comparable non-collapsible fixation assembly.

15 Claims, 19 Drawing Sheets

(56) References Cited

U.S. PATENT DOCUMENTS

| | | | |
|---|---|---|---|
| 3,727,610 A | | 4/1973 | Riniker |
| 4,006,740 A | | 2/1977 | Volkov et al. |
| 4,365,624 A | | 12/1982 | Jaquet |
| 4,383,488 A | * | 5/1983 | Macho et al. ............... 108/129 |
| 4,535,763 A | | 8/1985 | Jaquet |
| 4,628,922 A | | 12/1986 | Dewar |
| 4,768,524 A | * | 9/1988 | Hardy ........................ 606/54 |
| 5,087,258 A | * | 2/1992 | Schewior ................... 606/56 |
| 5,372,597 A | * | 12/1994 | Hotchkiss et al. .......... 606/56 |
| 5,403,319 A | | 4/1995 | Matsen et al. |
| 5,496,319 A | | 3/1996 | Allard et al. |
| 5,505,142 A | * | 4/1996 | Fink ........................... 108/129 |
| 5,681,272 A | * | 10/1997 | Lee ............................. 602/32 |
| 5,863,292 A | | 1/1999 | Tosic |
| 5,979,658 A | | 11/1999 | Allen et al. |
| 6,030,386 A | * | 2/2000 | Taylor et al. ................ 606/56 |
| 6,129,727 A | * | 10/2000 | Austin et al. ............... 606/56 |
| 6,328,737 B1 | | 12/2001 | Moorcroft et al. |
| 6,355,037 B1 | * | 3/2002 | Crosslin et al. ............. 606/57 |
| 6,550,404 B2 | * | 4/2003 | Stanford .................... 108/132 |
| 6,568,506 B1 | * | 5/2003 | Donnalley .................. 182/223 |
| D505,803 S | * | 6/2005 | Mason ...................... D6/406.6 |
| 6,966,404 B2 | * | 11/2005 | Meeker ....................... 182/33 |
| 7,100,519 B2 | * | 9/2006 | Tsai ........................... 108/132 |
| 7,308,858 B2 | * | 12/2007 | Lo et al. .................... 108/131 |
| 7,361,176 B2 | * | 4/2008 | Cooper et al. ............... 606/54 |
| 7,662,159 B2 | | 2/2010 | Brandigi |
| 7,815,586 B2 | * | 10/2010 | Grant et al. ................. 602/23 |
| 8,172,849 B2 | | 5/2012 | Noon et al. |
| 8,257,353 B2 | * | 9/2012 | Wong ........................ 606/59 |

| | | | |
|---|---|---|---|
| 2003/0009167 A1 | | 1/2003 | Wozencroft |
| 2004/0204668 A1 | * | 10/2004 | Polonchek ................ 602/32 |
| 2005/0043730 A1 | | 2/2005 | Janowski et al. |
| 2005/0061213 A1 | * | 3/2005 | Tsai ........................ 108/132 |
| 2005/0113829 A1 | | 5/2005 | Walulik et al. |
| 2005/0149018 A1 | * | 7/2005 | Cooper et al. ............ 606/54 |
| 2005/0251136 A1 | | 11/2005 | Noon et al. |
| 2006/0130718 A1 | * | 6/2006 | Lo et al. .................. 108/131 |
| 2006/0184169 A1 | * | 8/2006 | Stevens ................... 606/54 |
| 2007/0055234 A1 | | 3/2007 | McGrath et al. |
| 2007/0106193 A1 | * | 5/2007 | Davis et al. .............. 602/32 |
| 2008/0021451 A1 | * | 1/2008 | Coull et al. .............. 606/54 |
| 2008/0086122 A1 | | 4/2008 | Starr |
| 2008/0132817 A1 | * | 6/2008 | Vito ......................... 602/23 |
| 2008/0269741 A1 | * | 10/2008 | Karidis .................... 606/56 |
| 2009/0105621 A1 | * | 4/2009 | Boyd et al. ............... 602/3 |
| 2009/0124947 A1 | * | 5/2009 | Grant ....................... 602/23 |
| 2009/0177198 A1 | * | 7/2009 | Theodoros et al. ....... 606/56 |
| 2009/0187127 A1 | * | 7/2009 | Buckman et al. ........ 602/13 |
| 2009/0198235 A1 | * | 8/2009 | Steiner et al. ............ 606/57 |
| 2009/0275944 A1 | * | 11/2009 | Huebner et al. .......... 606/54 |
| 2010/0179548 A1 | * | 7/2010 | Marin ...................... 606/59 |
| 2010/0179605 A1 | * | 7/2010 | Branch et al. ............ 606/86 R |
| 2010/0191239 A1 | * | 7/2010 | Sakkers et al. ........... 606/59 |
| 2010/0234844 A1 | * | 9/2010 | Edelhauser et al. ...... 606/56 |
| 2010/0280516 A1 | * | 11/2010 | Taylor ..................... 606/59 |
| 2010/0305568 A1 | * | 12/2010 | Ross et al. ............... 606/56 |
| 2010/0312243 A1 | * | 12/2010 | Ross et al. ............... 606/56 |
| 2010/0331840 A1 | * | 12/2010 | Ross et al. ............... 606/54 |
| 2011/0118737 A1 | * | 5/2011 | Vasta et al. .............. 606/56 |
| 2011/0208187 A1 | * | 8/2011 | Wong ..................... 606/59 |
| 2011/0313419 A1 | * | 12/2011 | Mullaney ................ 606/56 |
| 2012/0303029 A1 | * | 11/2012 | Vasta et al. .............. 606/56 |

\* cited by examiner

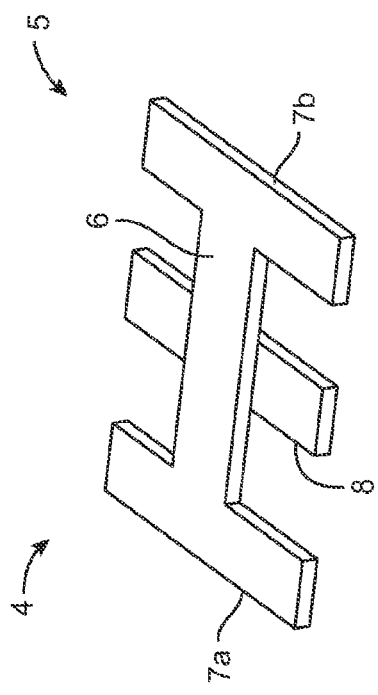
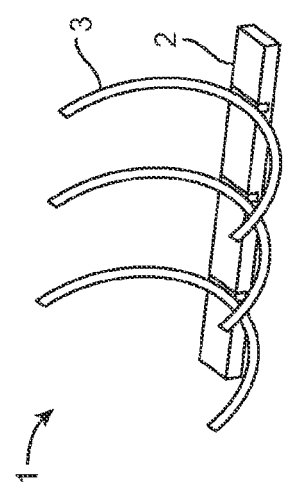
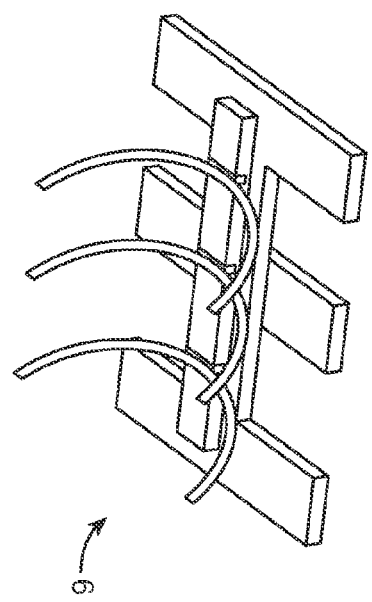
FIG. 1A
FIG. 1B
FIG. 1C

ORTHOPEDIC FIXATION SYSTEMS AND METHODS

CROSS-REFERENCES TO RELATED APPLICATIONS

The present application is a continuation-in-part of U.S. patent application Ser. No. 12/956,768, filed Nov. 30, 2010, the full disclosure of which is incorporated herein by reference.

BACKGROUND OF THE INVENTION

The present invention relates to orthopedic fixation systems, assemblies, devices and related methods for reduction of a fractured bone of a patient.

Reduction is a medical procedure to restore a fracture or dislocation to the correct alignment. When a bone fractures, the fragments lose their alignment in the form of displacement or angulation. For the fractured bone to heal without substantial deformity the bony fragments must be re-aligned to their normal anatomical position. Orthopedic surgeons attempt to recreate the normal anatomy of the fractured bone by reduction.

Fractured bone reduction or treatment can include use of fixation methods that can reinforce the fractured bone and keep it aligned during healing, including use of external devices or casts as well as internal devices such as rods, bone plates and/or fasteners. Under certain circumstances, a physician may decide that external fixation is the best treatment for a patient. Fixation with external devices and assemblies includes surgical techniques for setting bone fractures and/or for limb lengthening that was first used more than a century ago. Since that time, the technique has evolved from being used primarily as a last resort fixation method to becoming a main stream technique used to treat a myriad of bone and soft tissue pathologies.

In some cases, external fixation can be accomplished by placing pins or screws into the bone of a patient and securing the pins through the use of an external frame assembly positioned at least partially outside the body. During the treatment, the external frame can hold bone fragments at adjustable spacing and angles to create a desired overall bone length and angular disposition of the bone fragments. To connect the external fixation device to the bone, pins can be placed, for example, on either side of the break in the bone and pass through the skin and sometimes the muscles. Sometimes wires can also be used with the pins, or in place of pins, to secure the bone pieces. The pins and/or wires can hold the bone in place and anchor the fixator securely, while also avoiding damage to vital structures, allowing access to the area of injury, and meeting the mechanical demands of the patient and the injury. Treatment using external fixation can take about 6 weeks for a simple fracture, and up to one year or longer for a more complicated fracture.

As compared to other fixation methods, external fixation devices can provide numerous advantages. When compared with internal plates and intramedullary nails, for example, external fixators can cause less disruption of the soft tissues, osseous blood supply, and periosteum. Accordingly, external fixation devices can be useful for soft tissue management in the setting of acute trauma with skin contusions and open wounds, in chronic trauma where the extremity is covered in thin skin grafts and muscle flaps, and in patients with poor skin whose healing potential is compromised as in the case of rheumatoid disease, peripheral vascular disease, diabetes mellitus, and Charcot disease. In addition, the temporary nature of the pins and wires can provide bony stability in the setting of osteomyelitis where the presence of internal implants make eradication of infection more challenging. The ability to avoid putting fixation into the infected area is equally beneficial.

Unlike internal plates and intramedullary nails, external fixators also provide postoperative adjustability. This allows the extremity to be manipulated in the operating room to gain exposures to fracture fragments. In the situation of limb lengthening or deformity correction, gradual manipulation is possible with frame adjustment over time. As a result, external fixations have found use in pediatric fracture care where open physes preclude intramedullary nailing. Leg length discrepancy can also be reliably treated with circular and monolateral design fixators.

Despite these advantages, existing external fixation devices and assemblies still remain limited in their application for treatment of bone fractures. For example, while the devices known in the prior art can help provide valuable treatment of fractures, particularly in the surgical setting, existing devices can be somewhat cumbersome and limited in versatility. Thus, there is continued interest in providing improved external fixation devices that are more versatile and can be used, for example, as more ambulatory or portable devices.

BRIEF SUMMARY OF THE INVENTION

The present invention relates to orthopedic fixation systems, assemblies, devices and related methods for reduction of a fractured bone of a patient.

In one embodiment, the present invention provides orthopedic fixation systems including a primary fixation device and a base station. The base station can be configured to receive and reversibly couple with the primary fixation device in whole or in part, for formation of a more elaborate or more stabilized fixation or bone reduction assembly.

Systems further include frame components, e.g., rings, struts, rails, and/or braces, as well as bone-interface components, e.g., pins and/or wires. The frame components, for example, can be used by a healthcare provider to assemble the systems in a fashion to allow for varied levels of stabilization. In one embodiment, the primary fixation device can include an elongate base rail having a length and opposing distal and proximal end portions each removably couplable to a stand structure. The primary fixation device can further include one or more rings removably and slidably coupled to the base rail along the base rail length. The base station will generally have a surface stabilizing structure or arrangement, where the base station disposed on a working surface (e.g., surgical setting or table) can couple together with the primary fixation device and provide a stabilized combined assembly. For example, the base station can have a generally "H" shaped base frame that can include an elongate center support having a length and opposing distal and proximal end portions each presenting a lateral support. The systems of the present invention can further include bone-interface components that, for example, can be used to connect to a bone for medical procedures, such as fixation and/or reduction. In one embodiment, the bone-interface components can include fixing pins and wires.

The methods of using the systems of the present invention can include a variety of embodiments. In one embodiment, a method can include transporting a patient from a first point to a second point while the patient's bone is immobilized in a primary fixation device. The primary fixation device, in whole or in part, can be coupled together to a base station at the second point, e.g., while the patient's bone is immobilized.

In another embodiment, the methods can include providing an orthopedic fixation system having a primary fixation device and a base station, and then coupling or uncoupling the primary fixation device and the base station while a bone of a patient is fixed or reduced with the primary fixation device. In yet another embodiment, a method can include fixing or reducing a limb of a patient in a primary fixation device and coupling the primary fixation device to a base station while the patient's limb is constrained with the primary fixation device.

The present invention can further include sterilization kits and methods for sterilizing a patient's limb while immobilized in a fixation device and/or system. The sterilization kits can include a sterilizing container, a sterilization solution, or other parts for a kit that can provide sterilization. In one embodiment, a patient's limb can be sterilized after fixation or reduction of the limb in a primary fixation device by placing a sterilizing container around the limb and the device. The sterilizing container can be removed before or after coupling the primary fixation device to a base station.

The present invention also provides collapsible orthopedic fixation assemblies. In one embodiment, a collapsible fixation assembly includes end frames that are coupled with one or more cross beams. The collapsible fixation assembly is reconfigurable between a collapsed configuration in which the end frames are substantially aligned with the one or more cross beams and a deployed configuration in which the end frames are oriented transverse to the one or more cross beams and in which relative movement between the end frames and the one or more cross beams can be inhibited. The end frames are configured to support at least one bone-interface component, which is configured to constrain a bone of a patient. In the collapsed configuration, such fixation assemblies are more compact than in the deployed configuration, thereby, for example, making them more easy to store and transport as compared to comparable non-collapsible fixation assemblies.

The present invention provides methods for treating a fractured bone of a patient. In one embodiment, a method includes repositioning end frames relative to one or more cross beams from a collapsed configuration in which the end frames are substantially aligned with the one or more cross beams and a deployed configuration in which the end frames are oriented transverse to the one or more cross beams, inhibiting relative movement between the end frames and the one or more cross beams in the deployed configuration, and constraining at least one bone of the patient via at least one bone-interface component supported by at least one of the end frames.

For a fuller understanding of the nature and advantages of the present invention, reference should be made to the ensuing detailed description and accompanying drawings. Other aspects, objects and advantages of the invention will be apparent from the drawings and detailed description that follows.

BRIEF DESCRIPTION OF THE DRAWINGS

FIGS. 1A-C illustrate a primary fixation device, a base station, and an orthopedic fixation system, in accordance with an exemplary embodiment of the present invention.

DETAILED DESCRIPTION OF THE INVENTION

Figure 2A:
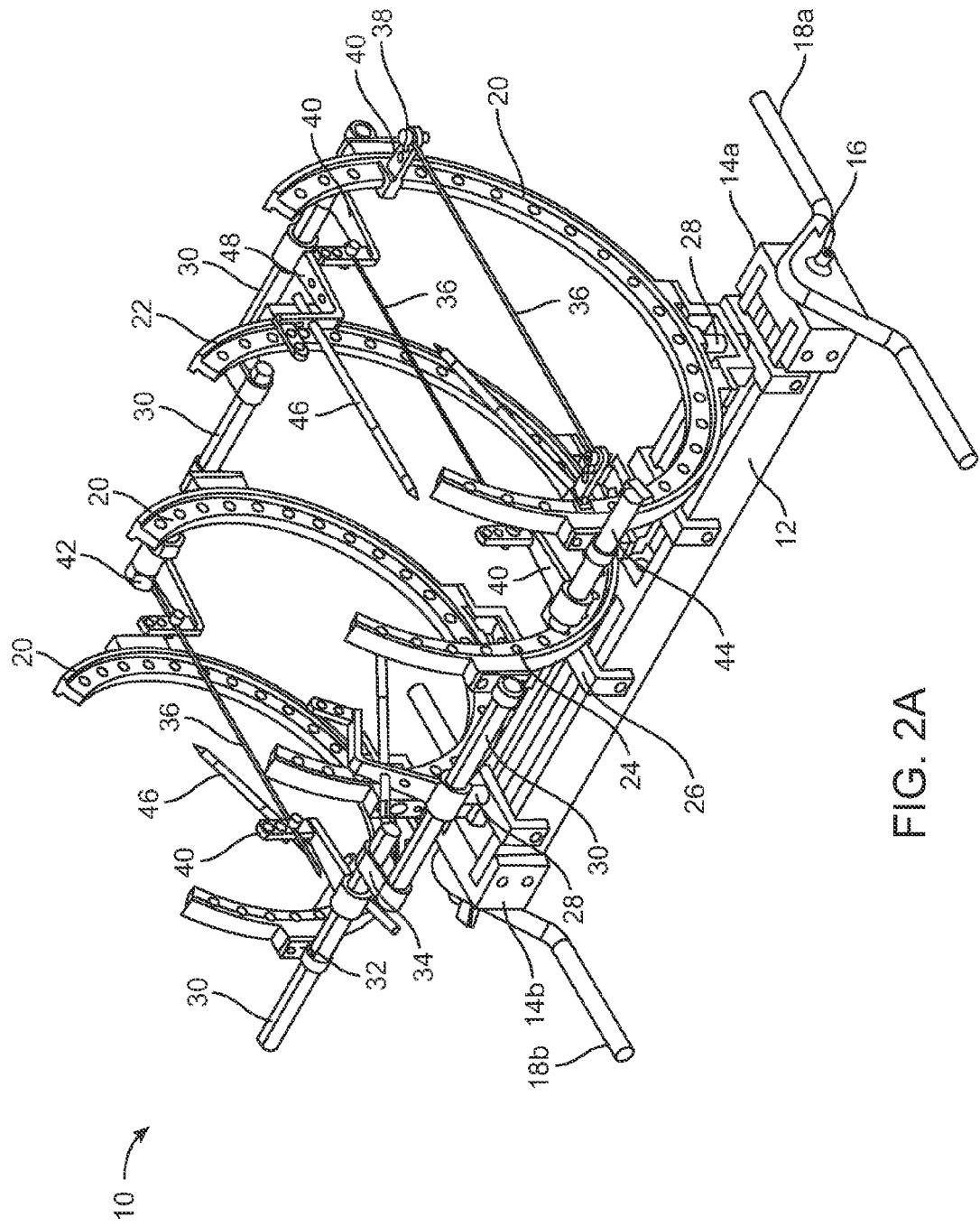
FIG. 2A illustrates a top-facing view of a primary fixation device, in accordance with an exemplary embodiment of the invention.

The present invention relates to orthopedic fixation systems, assemblies, devices and related methods for fracture reduction or fixation, as well as stabilizing a patient's limb for a reduction procedure.

Fixation Systems and Related Methods

Fracture reduction or fixation systems as described herein generally reference two main components: a primary fixation device and a base station. The primary fixation device generally includes an elongate base rail with one or more frame or bone-interface components disposed along the rail so as to provide some degree of adjustability or fracture reduction capacity. The base station couples together with the primary fixation device for increased stabilization and/or functionality of the combined assembly.

In use, fracture reduction in a patient may employ fixation system components in both an uncoupled stages as well as a stage where components (e.g., primary fixation device and base assembly) are coupled together during treatment. For example, the primary fixation device may be utilized for a more temporary and/or ambulatory stabilization of a patient, before the patient is transported to a more long-term or less transient setting. After an initial or first stage of reduction/fixation of the patient fracture with the primary fixation device, the device (e.g., in whole or in part) can be coupled together with a base station for further stabilization and fracture reduction. Thus, systems may find use in settings such as an emergency room or field setting, where the patient receives some degree of reduction of the patient with employment of the primary reduction device, followed by coupling of the primary reduction device (e.g., following patient transport or movement) to a surgical setting or operating room for more throughout fracture reduction and treatment.

Orthopedic fixation systems as described herein generally include frame structures that surround and/or extend along one or more bones to allow for stabilization of a fracture and/or reconstruction of bones and/or surrounding tissue. The systems of the present invention can include a variety of components that can be selected for a desired level of stabilization. Systems of the present invention can include at least two main components: a primary fixation device and a base station. As indicated, a primary fixation device can be configured with an elongate base rail and other frame or bone-interface components (e.g., rings and/or fixation pins, respectively) that can assist in stabilizing a bone (e.g., tibia, fibula, femur or humerus). The base station can include a base frame and can be further configured to receive and removably couple with the primary fixation device, which can also be configured to couple with the base station. Coupling the primary fixation device to the base station can be accomplished through a variety of ways. In certain embodiments, the primary fixation device can be wholly coupled to the base station without removing or replacing any components coupled to the primary fixation device. Alternatively, the primary fixation device can be partially coupled with the base station such that some of the components are replaced or modified to provide additional stabilization or other features that may be desired by a healthcare provider. A primary fixation device may initially wholly be coupled together with a base station, followed by adjustment or replacement of components of the primary fixation device.

For use, the systems of the present invention can be generally used for medical procedures that involve fixation and/or reduction of a patient's bone, including limb stabilization. The orthopedic fixation systems of the present invention can be applied to treat various bones or fractures, including bones/fractures of both upper and/or lower limbs, such as a bone in the leg or the arm. A leg bone can include a femur, a tibia, a fibula, or a combination thereof. An arm bone can include a humerus, a radius, an ulna, or a combination thereof. In some embodiments, a segment of a bone can be treated using a device of the present invention. In certain embodiments, the orthopedic fixation systems of the present invention can also serve as reduction devices for a fractured or dislocated bone. For example, the systems can be configured to provide open or closed reduction. For open reduction, bone fragments are exposed surgically to assist in restoring a fracture or dislocation. Closed reduction can manipulate the bone fragments without surgical exposure.

In certain notable aspects, the coupling relationship between the primary fixation device and the base station particularly can allow for increased portability and flexibility for stabilizing a bone, for example, at the scene of an accident or other environments in which portability is desired to keep the bone stabile before surgery in an operating room. The systems can also provide a greater versatility in use because the systems can be assembled to allow for different levels of stabilization of the bone. For example, in some situations, healthcare providers may desire more adjustable systems for mobility that can later be modified to increase stability upon arrival to a location that allows for such modifications. As described in more detail below, a primary fixation device can be assembled to include frame components that may allow for fixation or reduction of a bone in situations that involve more temporary, mobile stabilization. Upon initial treatment of a patient, the stabilization device can provide less stability, and thus better portability, than, e.g., the greater stability that may be desired for some operating room situations.

The orthopedic fixation systems described herein can include one or more of a variety of components for the primary fixation device and/or base station. As noted, systems typically form a frame-like assembly that is worn or disposed outside the body and along the bone or fracture site. Thus, systems herein will include certain frame structures or components, such as, e.g., rings, rails, braces, struts, arms, etc. Systems will often make use of stabilization or fixation rings, which can couple to other system components (e.g., base rail) for formation of a frame-like structure and facilitate stabilization of a bone in a reduction procedure. In one embodiment, frame components of a primary fixation device will include one or more rings each coupled along an elongate base rail.

In addition to frame components, the systems can further include certain components for interfacing between the system outer frame structure and the patient's bone or fragments ("bone-interface components") to allow manipulation, positioning, or re-alignment of bone fragments for reduction. Bone interface components can include, for example, various types of orthopedic pins, rods, screws, shafts, wires, and the like that can connect to a bone, e.g., between a frame component and the patient's bone/fragment for positioning or reduction as described. Bone-interface components are commonly coupled to frame ring structures and can be coupled to various frame components, including rings, struts, rails, arms, etc.

As described herein, the systems can include a multitude of frame components, such as rings and base rails. The rings can be of any size and/or shape suitable for use with the systems, devices, and methods of the present invention. The rings can include full rings and/or partial rings, such as half or three-quarter rings, and/or U-shaped plates. Rings can further include mechanisms for mounting other bone-interface components. For example, rings can include holes or ribs that can be coupled with additional mounting components, such as brackets or other structures that allow for coupling connectors to interface with bone. In certain embodiments, the rings can be removably and/or slidably coupled to an elongate base rail of a primary fixation device. Coupling of the rings to the base rail can be achieved using several different mechanisms, and the base rails of the primary fixation devices can be of any suitable size or shape. In some embodiments, a base block or other slidable structure that fits to the base rail can slide along the length of the rail so as to allow horizontal placement of the rings in relation to a bone. Once in a desired position, the base block can be tightened to the base rail to remain in the desired position. Relative height of the rings in relation to the base rail can be further adjusted with an adjustable pedestal that can couple with the ring. The adjustable pedestal can further removably and/or slidably couple to a base block via a post, and the pedestals can slide along the posts to adjust the height of the ring in a direction that is, e.g., orthogonal to the length of the base rail. Similar to the base block, the pedestals can be held in a rigid position by a variety of mechanisms, such as screw tightening. In certain embodiments, the rings can be further supported by ring supports that can couple to the base rail or the base station. The ring supports, for example, can be used after the primary fixation device is coupled to the base station and a healthcare provider desires increased stabilization.

Struts used in the present invention may have any suitable dimension of size or shape to, for example, provide for stabilization and/or mounting of various bone-interface components or other frame components. Struts can be elongate and substantially linear in shape or a whole or part of the strut can be bent (e.g., angular and/or curved). In some embodiments, a strut can be a member of a set of struts, in which each strut can be the same size or of different sizes. The set of struts can include struts of the same and/or different diameter, the same and/or different maximum (and/or minimum) length, and/or the same and/or different angular adjustability. Distinct struts, of the same or different size/adjustability, can be marked as distinct. For example, the struts may include indicia, such as alphanumeric characters, distinct colors, removable (or permanent) colored bands, etc. In some embodiments, the indicia can be used by a healthcare professional to choose specific struts having a desired shape and/or stiffness for a particular stabilization procedure. In certain embodiments, struts can also include one or more movable joints that can, e.g., permit relative (internal) translational or pivotal motion of portions the strut. In some embodiments, the joint can allow a twisting motion about an axis parallel to a long axis defined by the strut. In addition, a joint can also permit a bending motion(s) about an axis (or axes) transverse to the long axis of the strut. The joint may be a hinge joint, a ball-and-socket joint, and/or a combination thereof, among others.

The struts can be secured by any suitable mechanism to primary fixation devices, base stations, rings, other struts, or other components of the systems of the present invention. For example, a strut can be fastened at several points along a set of rings that are removably and slidably coupled to an elongate base rail of a primary fixation device. Alternatively, one strut can be coupled at one end to one ring and at the other end to a second ring. The locations and orientations of the struts in relation to rings, or other components, can be dependent on the particular application of the struts for stabilizing the bone in an orthopedic fixation system of the present invention.

Additional support components, such as braces, can be coupled to the base station, the primary fixation device, and/or other components so as to increase or decrease the stabilization level of the orthopedic fixation systems. In certain embodiments, the braces can provide additional stabilization support when a primary fixation device is coupled to a base station. Braces can include various components configured to facilitate support for the systems as well as to provide adjustment capability for a user. Suitable brace components can include rod supports, hinges, adjustment handles, joints, etc. The braces can have a configuration that can be adjusted in a variety of ways, such as in length, angle, height, etc. In some embodiments, the braces can include at least one joint or hinge to permit internal relative motion among various components of the brace. Other components, such as adjustment handles, can be configured to allow a healthcare provider to adjust the size and/or shape of the brace as well as the way the brace can couple with other system components, such as the base station.

In addition to the frame components, base station, and/or primary fixation device, the present invention includes bone-interface components that can be connected to a bone. Suitable bone-interface components can include fixation pins, wires, screws, nails, plates, rods, bolts, staples, hooks, clamps, and the like, and/or a combination thereof. The bone-interface components can extend into bone, through bone, and/or around bone, etc. Furthermore, the bone-interface components can be slidably engaged with bone and/or fixed in relation to bone (e.g., threaded into bone). In some embodiments, the bone-interface components can extend from a frame component, e.g., a ring, to bone, or from a frame component to bone and then back to the same frame component. In other embodiments, a bone-interface component can extend from a frame component to bone and then to a different frame component. Each frame component can be connected to bone via the same or different type of mechanism.

In general, the frame components and/or bone-interface components can be coupled (e.g., permanently or removably coupled) to other components through a variety of ways. The coupling mechanisms for the systems of the present invention can generally include coupling mechanisms, such as fasteners, screws, nuts, brackets, and/or bolts, as well as other ways to attach various components, such as welding, gluing, tying, etc. In addition, rings can be removably and slidably coupled to an elongate base rail of a primary fixation device. Fixing pins and/or wires can be independently and/or removably coupled to the rings. Alternatively, the fixing pins and/or wires can be independently and/or removably coupled to components that are coupled to the rings or to the base. Coupling additional components to various parts of the assembly can depend on several factors, such as the bone needed fixation and/or reduction or, e.g., the placement of a fracture in the bone.

As provided in more detail below, representative aspects of embodiments of systems, devices, components and methods of the present invention are described with reference to the identified figures.

FIGS. 1A-C provide an exemplary orthopedic fixation system of the present invention. As shown in FIG. 1A, the primary fixation device 1 can include an elongate base rail 2 having a length and opposing distal and proximal end portions. One or more rings 3 can be removably and slidably coupled to the base rail 2 along the base rail length. The primary fixation device 1 will enable some degree of fracture reduction capacity, and may include any number of further components such as frame components as well as bone interface components.

A fixation system further includes a base station, that will include one or more surface stabilization components such that the base station coupled together with a primary fixation device can be stably positioned on a surface for fracture reduction and treatment of a patient. As depicted in FIG. 1B, in one embodiment, the base station 4 can have a generally "H" shaped base frame 5 that includes an elongate center support 6 having a length and opposing distal and proximal end portions each presenting a lateral support 7a,b. The base station 4 can optionally include an additional cross support 8 that can be positioned at an angle, e.g., orthogonally, along the center support 6, e.g., in middle of the center support. As shown in FIG. 1C, the base frame 5 can be further configured to receive and removably couple with components of the primary fixation device 1 such that the elongate base rail 2 is disposed substantially along the length of the base frame center support 6. As further depicted in FIG. 1C, an orthopedic fixation system 9 of the present invention can include the primary fixation device 1 removably coupled to the base station 4.

Figure 2B:
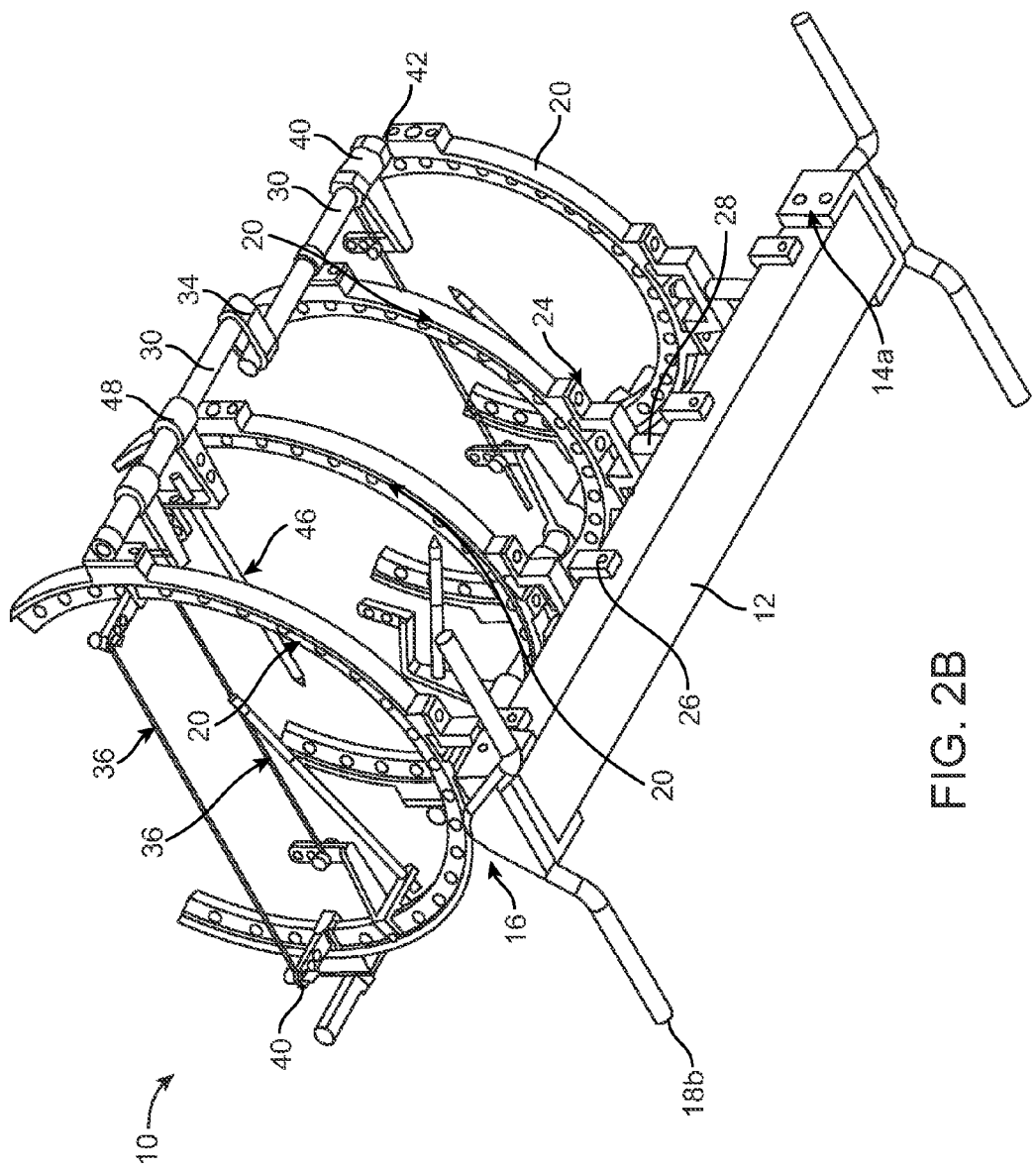
FIG. 2B shows a bottom-facing view of a primary fixation device, in accordance with an exemplary embodiment of the invention.

A primary fixation device according to an embodiment is illustrated with reference to FIGS. 2A and 2B. FIG. 2A illustrates a top-facing view and FIG. 2B illustrates a bottom-facing view of a primary fixation device 10 in accordance with an exemplary embodiment of the present invention. The primary fixation device 10 includes an elongate base rail 12 and a detachable base member 14a and 14b. In certain embodiments, the detachable base member 14a and 14b can be used to facilitate coupling a primary fixation device to a base station, as described below. The elongate base rail 12 has a length and opposing distal and proximal end portions, each removably couplable to a stand structure 18a and/or 18b. The stand structures 18a and 18b can be coupled at each end of the elongate base rail 12 with a fastener 16, and its relative dimensions to the elongate base rail 12 can, for example, can depend on the size of the limb being treated or the amount of support necessary for adequate stabilization. The primary fixation device 10 can include one or more rings 20 that can be selected to have the same or different shape and/or diameter. The rings 20 can include full rings and/or partial rings, such as half or three-quarter rings, and/or U-shaped plates. The rings 20 can also include holes 22 for coupling additional components to the rings 20. Each ring 20 can be removably and/or slidably coupled to the elongate base rail 12 along the base rail length, for example, by an adjustable height pedestal 24 that is coupled to a base block 26 with a post 28. The rings 20 can be further connected together with one or more struts 30 that can, for example, be configured to provide load-bearing support. A ring 20 can be attached to a strut 30 with a fastening member 32. The struts 30 can be further coupled together by a coupling member 34, which can, e.g., increase the stability of the device 10. At least one wire 36 can also be coupled to the device 10 by several ways to allow, e.g., for fixation of a bone. As shown in the exemplary embodiment, the wire 36 can be coupled with a bolt member 38 to a bracket 40, which can be coupled to a strut 30 and optionally held in place with a nut 42. Alternatively, the bracket 40 can be coupled to a ring 20. Also, a wire 36 can be coupled to a bracket 40, which can be coupled to an extension bar 44. In addition or in place of a wire 36, one or more fixing pins 46 can be included in the device 10. As shown, a fixing pin 46 can be coupled to a strut 30 by a flag member 48. It will be appreciated that coupling and positioning of the fixing pins 46 and/or wires 36 will depend on, for example, the type and size of the bone being treated and/or the location of the fracture.

Figure 3:
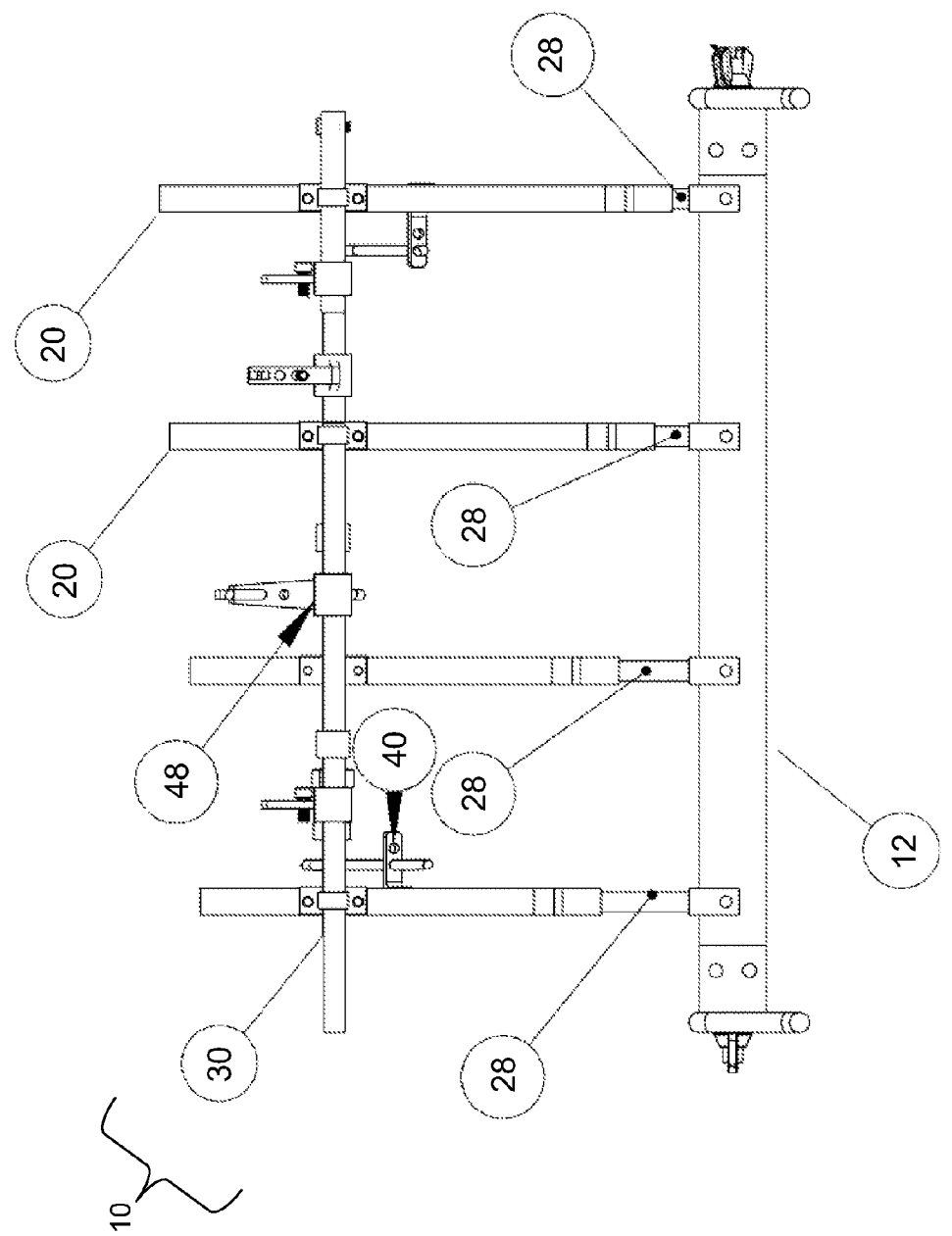
FIG. 3 shows a side view of a primary fixation device in accordance with an exemplary embodiment of the present invention.

FIG. 3 shows a side view of the primary fixation device 10 in accordance with an exemplary embodiment of the present invention. It is noted that the primary fixation device 10 can be configured to allow for increased adjustability that may be necessary for mobility and transport. As shown in this embodiment, the rings 20 of the device 10 can be positioned at different heights on the posts 28, which can be removably and slidably coupled to the elongate base rail 12. This height adjustability can further facilitate positioning of flag members 48 and/or brackets 40 in a straight line orientation, as shown by the orientation of the struts 30. In this embodiment, struts 30 can be positioned to be parallel to an axis along the length of the elongate base rail 12. Alternatively, the height can be adjusted to allow use of rings 20 with differing or the same diameters. For example, the diameters of the rings can decrease over the length of the elongate base rail 12 so as to allow for fixation of a limb having a decreasing diameter over its length, e.g., a leg. The rings 20 can also be positioned at a variety of angles relative to an axis along the length of the elongate base rail 12. As shown, the rings 20 are oriented orthogonally to the axis along the length of the elongate base rail 12.

Figure 4:
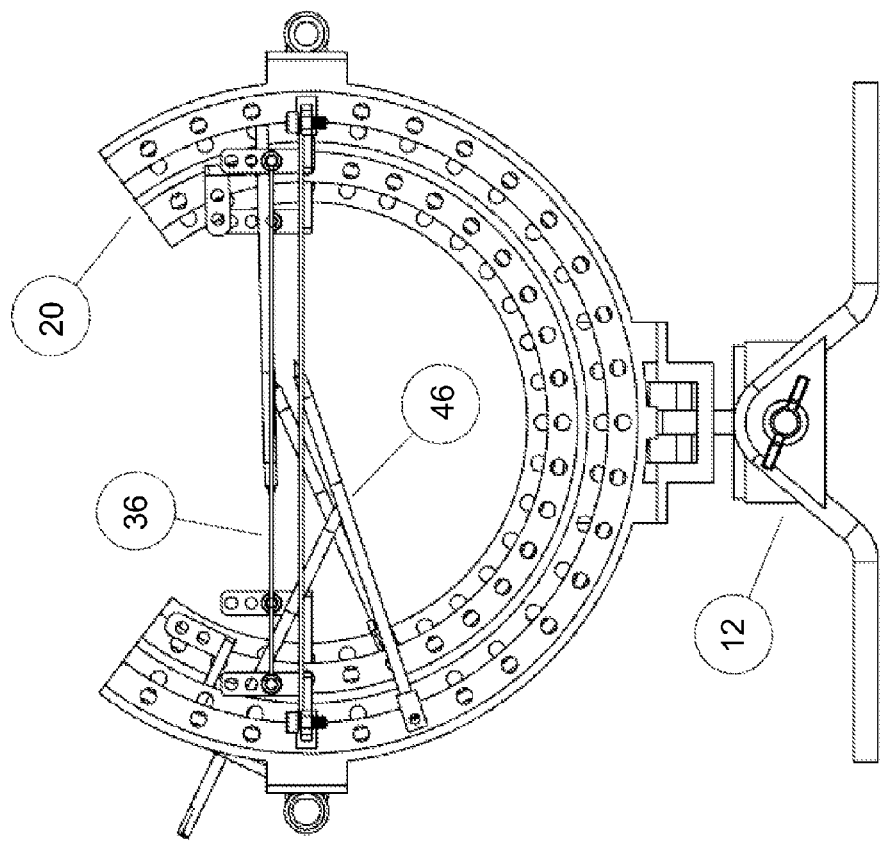
FIG. 4 illustrates a view down the length of a primary fixation device, according to an exemplary embodiment of the present invention.

FIG. 4 illustrates a view down the length of the primary fixation device 10 from one end of the elongate base rail 12, according to an exemplary embodiment of the present invention. As illustrated, the rings 20 can be positioned in seriatim down the axis of the elongate base rail 12. In addition, the fixing pins 46 and wires 36 can be positioned so as to intersect at a focal region near the center of the rings 20 that is typically located in the vicinity of a patient's limb placed in the assembly for stabilization. The position of each fixing pin 46 can be adjusted so as to allow for fixation of a bone of a patient within the rings 20 coupled to the elongate base rail 12.

Figure 5:
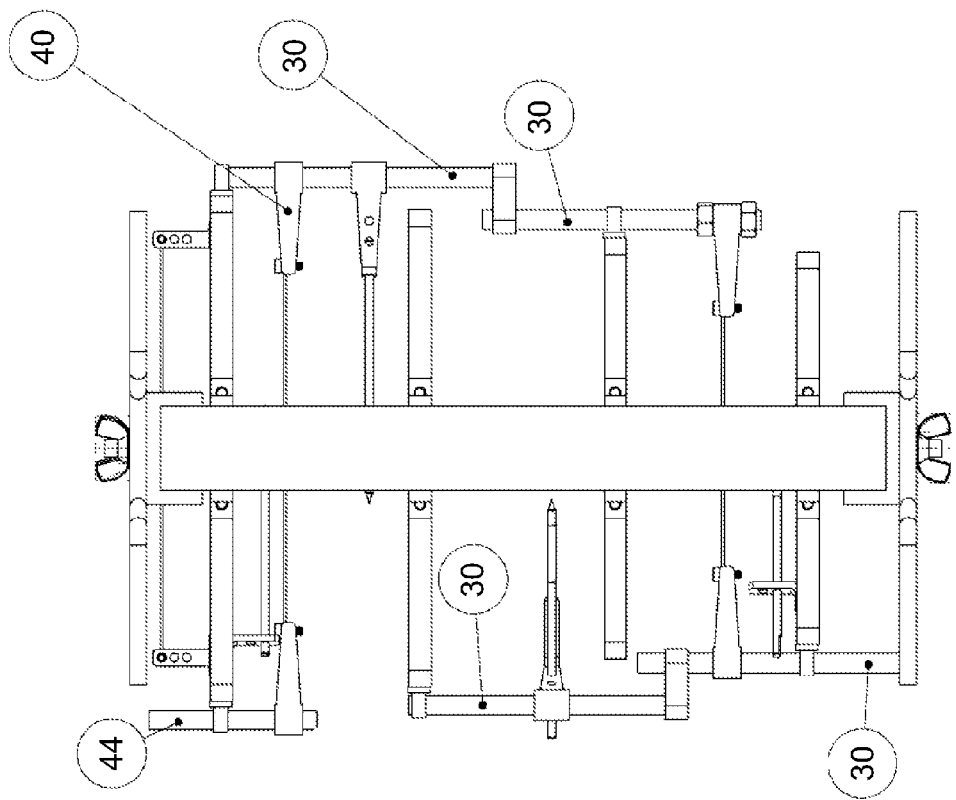
FIG. 5 shows a bottom view of a primary fixation device in accordance with an exemplary embodiment of the present invention.

FIG. 5 shows a bottom view of the primary fixation device 10 in accordance with an exemplary embodiment of the present invention. As shown, the struts 30 and the extension bar 44 can be positioned so as to be parallel to an axis along the length of the elongate base rail 12. The wires 36 and fixing pins 46 can be oriented in any angle that may be necessary to allow for fixation of the bone of the patient. For example, wires 36 coupled to brackets 40 can be positioned orthogonally to the struts 30. In addition, fixing pins 46 can also be positioned to be orthogonal to the axis along the length of the elongate base rail 12. It is also envisioned that each end of a wire 36 can be coupled to different rings 20 in the device 10.

In other embodiments, the present invention also provides orthopedic fixation systems including a primary fixation device and a base station. In some embodiments, the primary fixation devices can be transformed from a portable device to stationary devices by coupling to a base station configured to allow for increased stabilization of a bone of a patient. In certain embodiments, the primary fixation devices can be wholly or partially coupled with the base stations in a variety of ways. For example, a primary fixation device can be wholly coupled a base station such that all of the components in the primary fixation device are used upon incorporation into the base station. Alternatively, certain components and elements of the primary fixation device can be replaced with other components upon coupling with the base station. In an exemplary embodiment, the elongate base rail of a primary fixation device can be coupled to a base station including a generally "H" shaped base frame having an elongate center support having a length and opposing distal and proximal end portions each presenting a lateral support. The base frame can optionally include a support member that intersects the elongate center support at an angle, e.g., orthogonally, to provide additional stabilization to the assembly. In addition, rings of the primary fixation device can be coupled to one or more ring supports, which in turn can be coupled to one or more support members to provide for stabilization of a patient's limb.

Figure 6:
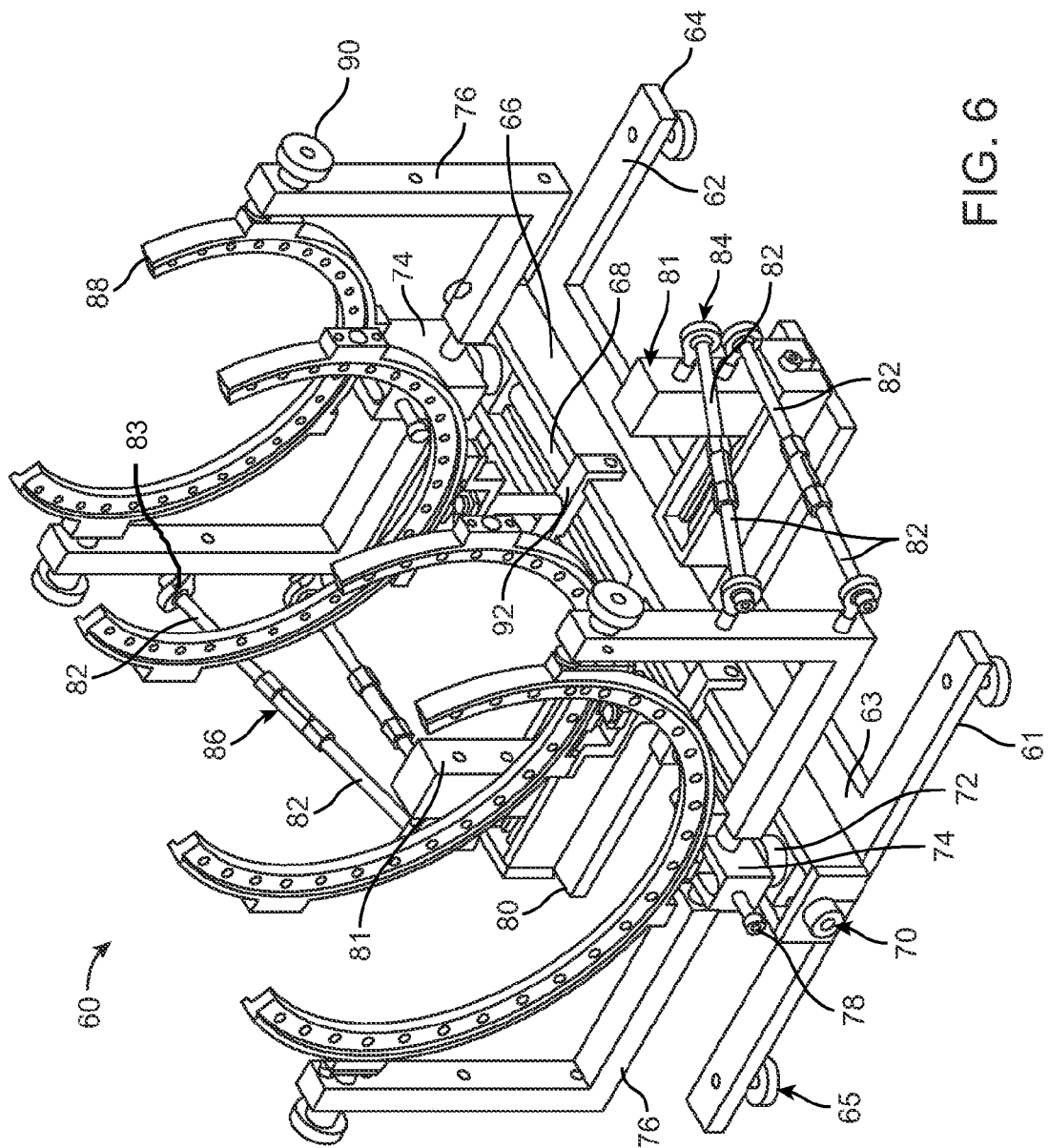
FIG. 6 illustrates a top-side view of an orthopedic fixation system in accordance with an exemplary embodiment of the invention.
Figure 7:
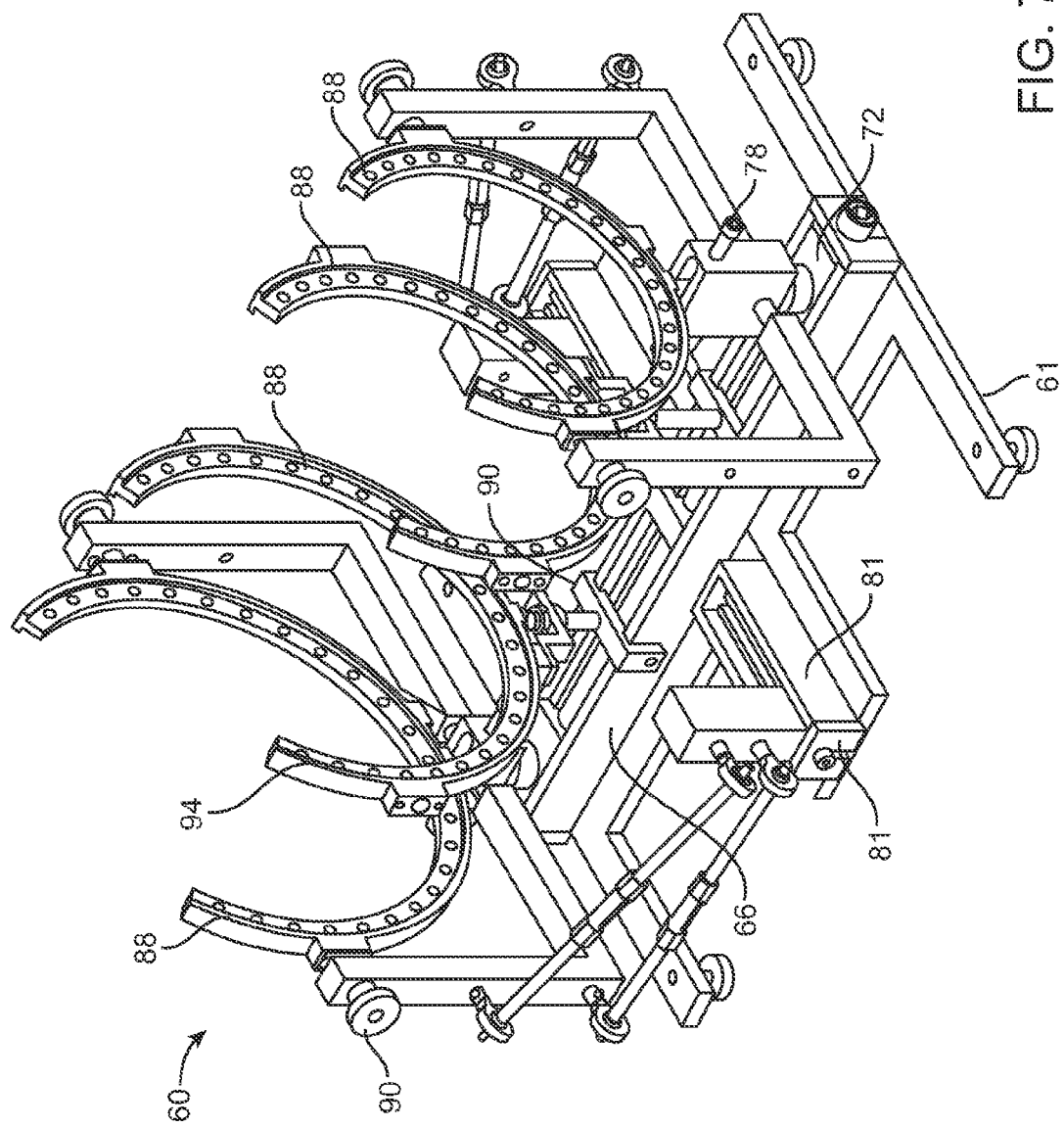
FIG. 7 illustrates another top-side view of an orthopedic fixation system in accordance with an exemplary embodiment of the invention.

FIGS. 6 and 7 illustrate different top-side views of an orthopedic fixation system 60 in accordance with an exemplary embodiment of the invention. The orthopedic fixation system 60 can include base station 61 having a generally "H" shaped base frame 62 comprising an elongate center support 63 having a length and opposing distal and proximal end portions each presenting a lateral support 64. The base station 61 can be adjusted with one or more leveling posts 65, e.g., coupled to each lateral support 64. As shown, certain components of the primary fixation device 10 (as described in more detail above) can be coupled to components of the base station 61. For example, an elongate base rail 66 (reference number 12, as described above) having a length can be coupled to the base station 61, which, for example, increases the stability of the assembly and allows for fixation in, e.g., an operating room. In certain embodiments, the elongate base rail 66 couples to the base station 61 having a generally "H" shaped base frame 62 that is configured to receive and removably couple with a primary fixation device 10 described above such that the elongate base rail 66 is disposed substantially along the length of the base frame center support 63. In some embodiments, the elongate base rail 66 can be composed of several different components. For example, the elongate base rail 66 can include a rod member 68 that is positioned along the center axis of the elongate base rail 66. The elongate base rail 66 can also include a fastening member 70 on one or both of opposing distal and proximal end portions of the elongate base rail 66. In certain embodiments, the fastening member 70 can replace the detachable base member 14 of the primary fixation device 10 described above. Additional components that can be replaced include one or more of the base blocks 26, posts 28, and adjustable height pedestals 24 described above. As shown, for example, the elongate base rail 66 can also include a bar-nut base 72 in the vicinity of the opposing distal and proximal end portions of the elongate base rail 66. A hinge base 74, which can be coupled to a ring support 76, can be coupled to the hinge base 74. The hinge base 74 can further include a tightening member 78. The ring support 76 can provide for additional stabilization and coupling to the base station 61. As shown, the base frame 62 can further include a cross support 80, which can be removably coupled with a support tower structure 81 that can be further coupled to one or more of the ring supports 76. In certain embodiments, a brace 82 can be coupled to the support tower structure 80 and/or to the ring support 76 by a coupling member 83. As shown here, a brace 82 can include rod supports 84 that can be adjusted relative to each other by an adjustment handle 84. The orthopedic fixation system 60 can further include one or more rings 88 that can be coupled to the ring support 76 with a fastener 90. Alternatively, one or more rings can be coupled to a base block 92, which is further coupled to the elongate base rail 66 similar to the embodiments discussed above for the primary fixation device 10. Similar to the exemplary embodiment in FIGS. 2A and 2B, additional fixing pins, wires, and other components can be coupled to the assembly 60 to facilitate treatment of a patient. For example, a bracket can be coupled to a hole 94 in a ring 88 to provide for coupling of a fixing pin or wire. In some embodiments, the orthopedic fixation system 60 can include the same fixing pins and/or wires that were inserted when the patient's bone was first reduced or fixed in the primary fixation device 10, described above.

In certain embodiments, two braces 82 can be coupled together by a brace coupling member 86.

Figure 8:
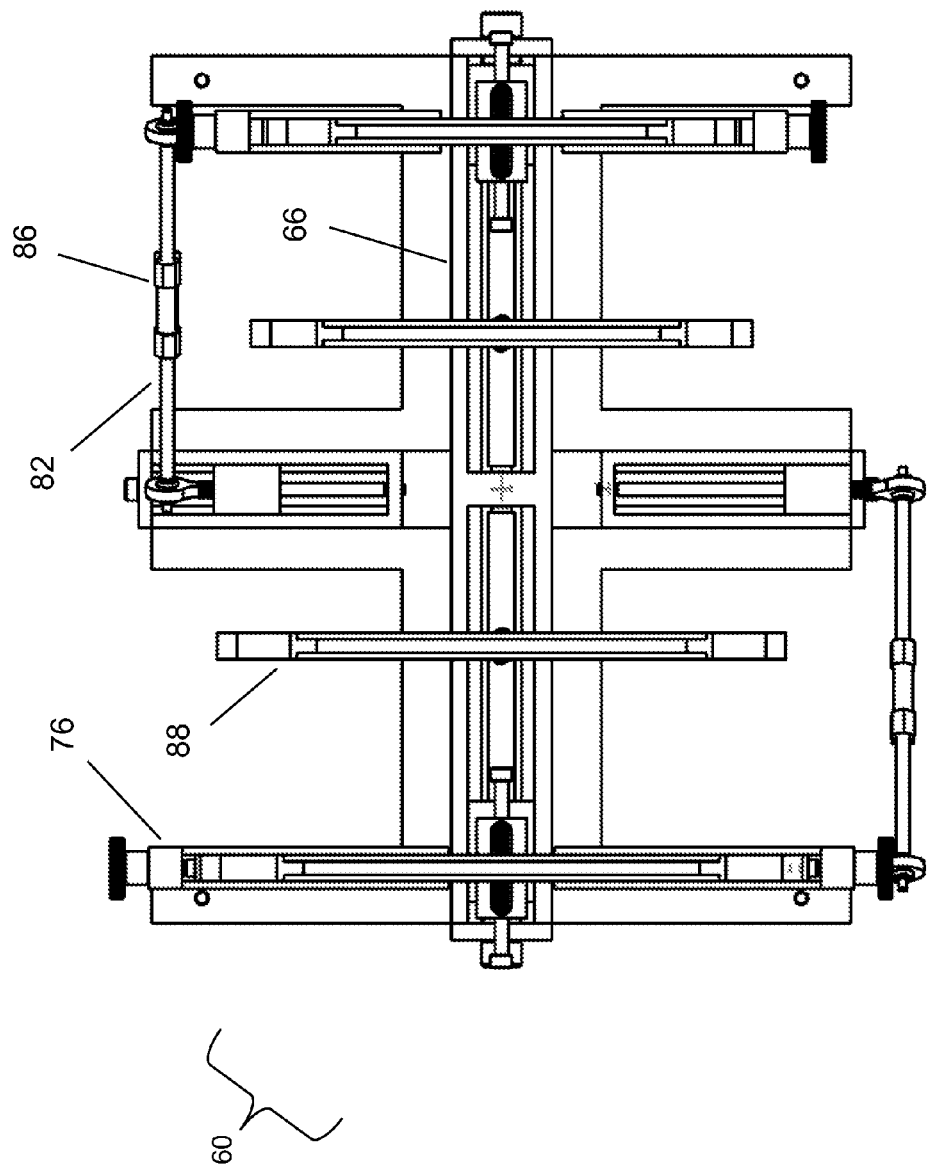
FIG. 8 shows a top view of an orthopedic fixation system in accordance with an exemplary embodiment of the invention.

FIG. 8 shows a top view of an orthopedic fixation system 60 in accordance with an exemplary embodiment of the invention. The various components of the assembly 60 can be positioned in a variety of angles and/or orientations, such as the orthogonal and/or parallel orientations shown. For example, the rings 88, the ring supports 76, and the cross support 80 can be orthogonal to an axis along the length of the elongate base rail 66. In this particular embodiment, the braces 82 are aligned to be parallel to the axis along the length of the elongate base rail 66. In addition, each brace 82 can be positioned on different sides of the base station 61 so as to provide additional cross support for stabilizing a patient's limb in the assembly 60.

Figure 9:
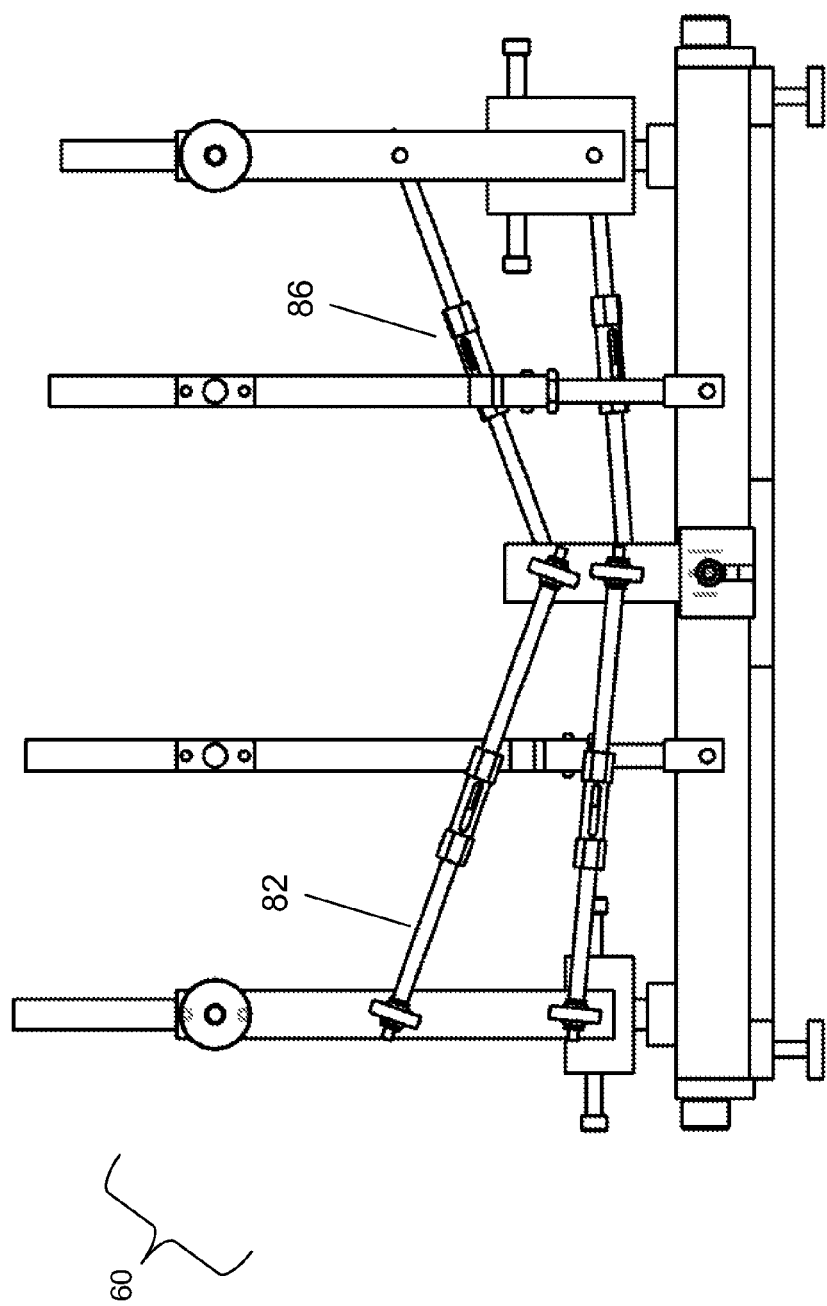
FIG. 9 illustrates a side view of an orthopedic fixation system in accordance with an exemplary embodiment of the invention.

FIG. 9 illustrates a side view of an orthopedic fixation system 60 in accordance with an exemplary embodiment of the invention. As shown, the cross support 80 can be positioned in a central location of the assembly 60, which will generally correspond to the placement of a patient's limb in the assembly 60. In addition, the braces 82 can be positioned at a variety of angles and heights. One of ordinary skill in the art will appreciate that positioning braces 82 can be arranged in a manner to provide maximum support to the assembly 60.

Figure 10:
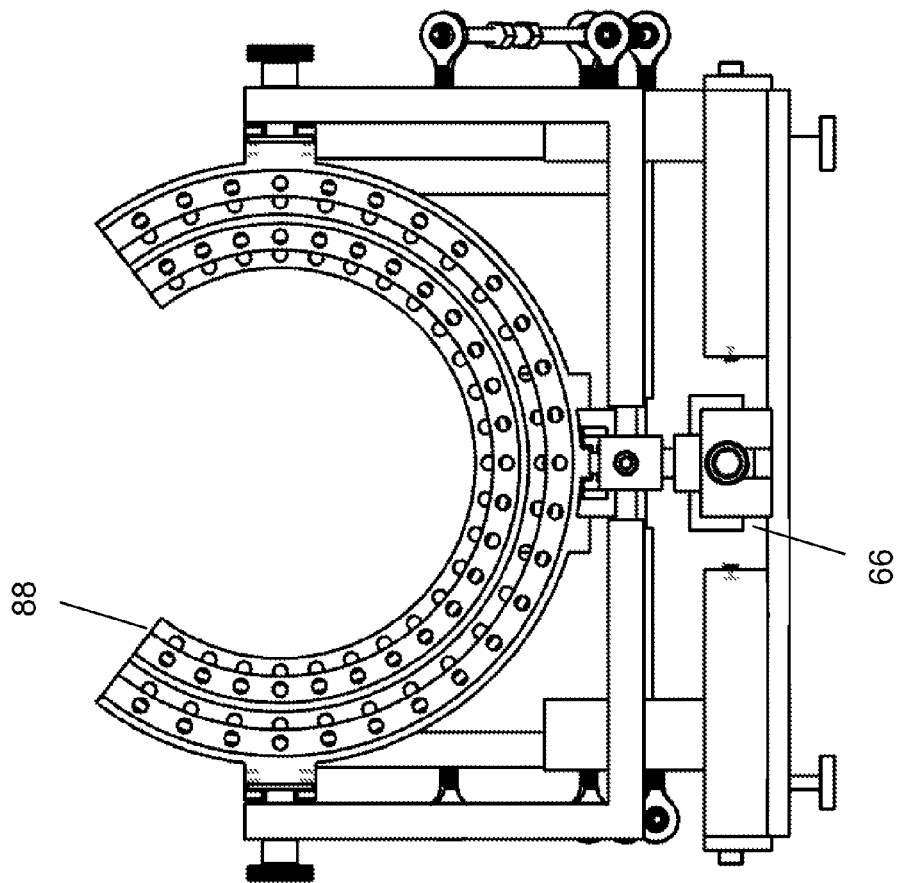
FIG. 10 illustrates a view down the length of an orthopedic fixation system, according to an exemplary embodiment of the present invention.

FIG. 10 illustrates a view down the length of the orthopedic fixation system 60 from one end of the elongate base rail 66, according to an exemplary embodiment of the present invention. As shown, the rings 88 can be positioned in seriatim down the length of the elongate base rail 66. The rings 88 can be selected to have a diameter so as to allow positioning of a limb in the central region of the rings 88. Wires and fixing pins, as provided e.g., in FIGS. 2A and 2B above, can then be positioned to allow for fixation of a limb during surgery. In some embodiments, the orthopedic fixation system 60 can include the same fixing pins and/or wires that were inserted when the patient's bone was first reduced or fixed in the primary fixation device 10 described above.

Structures, devices, and assemblies of the present invention will not be limited to any particular construction materials or compositions. Materials and compositions of the invention can include any variety of metals, alloys, polymers, and the like, alone or in combination, that are commonly used or generally suitable for use in medical or surgical applications. Extraction devices and components thereof may be made from conventional non-absorbable, biocompatible materials including stainless steel, titanium, alloys thereof, polymers, composites and the like and equivalents thereof.

In yet other embodiments, the present invention provides methods of using the devices and assemblies described herein. In an exemplary embodiment, the present invention provides a method of using an orthopedic fixation system can include transporting a patient from a first point to a second point while the patient's bone is immobilized with the primary fixation device and then coupling the primary fixation device to the base station at the second point while the patient's bone is immobilized with the primary fixation device. Other uses can include methods of using an orthopedic fixation system that include providing the orthopedic fixation system having a primary fixation device and a base station and coupling or uncoupling the primary fixation device and the base station while a bone of a patient is fixed or reduced with the primary fixation device. In yet other embodiments, a method of fixing or reducing a limb of a patient can include fixing or reducing a limb of a patient in a primary fixation device and coupling the primary fixation device to a base station while the patient's limb is constrained with the primary fixation device.

In yet another embodiment, the present invention provides a method for sterilizing a limb of a patient before an operation in which, for example, the primary fixation device is wholly or partially coupled together with the base station. In one embodiment, the present invention provides a method of sterilizing a limb of a patient positioned in an orthopedic fixation system that includes fixing or reducing the limb of the patient in a primary fixation device, placing a sterilizing container comprising a sterilization solution around the limb and the device, and removing the sterilization container such that the limb of the patient can be further stabilized by coupling the primary fixation device to a base station.

Figure 11:
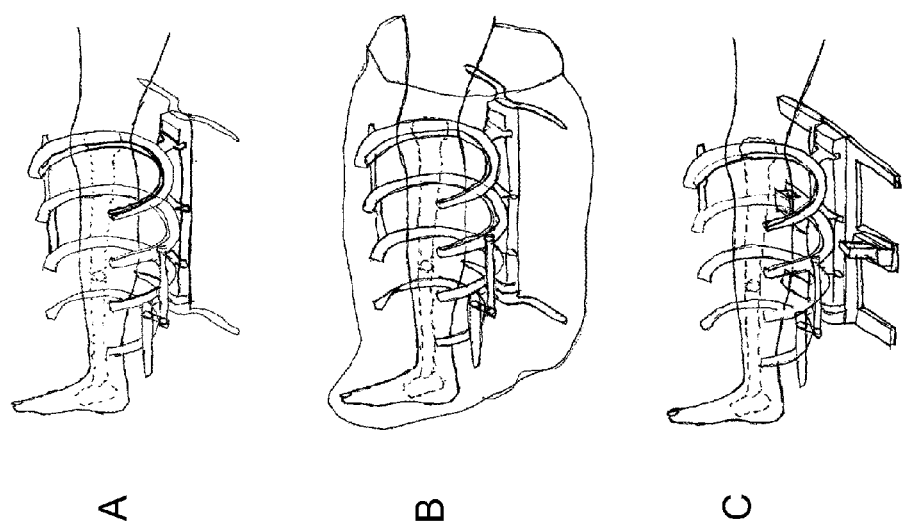
FIGS. 11A-C illustrate an exemplary method for sterilizing a patient's limb while being stabilized in an assembly of the present invention.

As illustrated in FIG. 11 A-C, the primary fixation devices of the present invention can be used for fixation and/or reduction of a patient's limb, e.g., a leg, under non-sterile conditions (FIG. 11A). As shown in FIG. 11B, a sterilizing container (e.g., a bag or other container providing sterilization conditions) can be placed around or in the vicinity of the patient's limb after temporary stabilization. The sterilizing container can be placed on or around the limb of the patient for a sufficient time period, such as the period between initial temporary stabilization until the patient arrives in an operating room for further treatment. After removal of the sterilizing container, the patient's limb can be positioned in a base station for treatment, such as for an operation (FIG. 11C). In certain embodiments, the orthopedic fixation systems of the present invention can further include a sterilization kit that can include a sterilizing container and a sterilization solution, such as, e.g., iodine, alcohol, or another liquid, gel, or other compound capable of sterilization.

One or more structures as described herein may be provided in the form of a kit. A kit may be assembled for portability, facilitating use in a surgical setting, and the like. This kit typically includes an orthopedic fixation system of the present invention, and the orthopedic fixation system may be provided in a fully assembled, partially assembled, or non-assembled configuration. As indicated, a device of the present invention may be configured or of a design that one or more components of the fracture reduction system have a limited or single use, or are replaceable. As such, a kit can include a fracture reduction device or assembly with one or more replacement components, such as one or more replacement primary fixation devices, base stations, or components thereof. A kit may include pre-sterilized components or device(s), as well as sterilized packaging.

The components of the present invention may be sterilized (and will generally be sterilizable) by any of the well known sterilization techniques, depending on the type of material. Suitable sterilization techniques include heat sterilization, radiation sterilization, chemical/gas sterilization, and the like.

Collapsible Fixation Assemblies and Related Methods

Collapsible fixation assemblies as described herein generally reference fixation assemblies that are reconfigurable between a collapsed configuration and a deployed configuration. In the collapsed configuration, a fixation assembly is more compact and thus easier to store and transport. From the collapsed configuration, the fixation assembly can be reconfigured to a deployed configuration for use in constraining one or more bones of a patient. The collapsible fixation assemblies can include any suitable number of suitable bone-interface components, such as the bone-interfacing components as described herein.

Figure 12A:
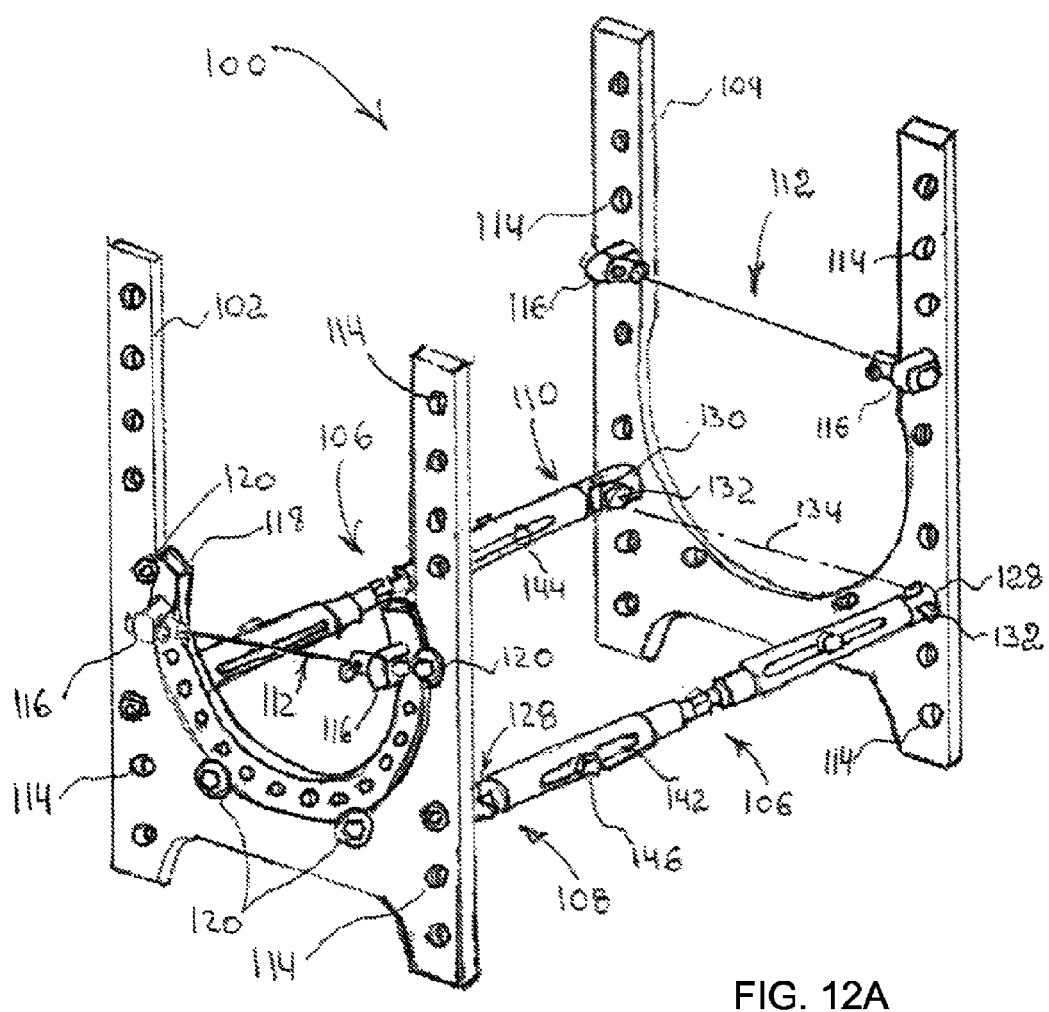
FIGS. 12A-B show perspective views of a collapsible orthopedic fixation assembly in a deployed configuration, in accordance with an exemplary embodiment of the invention.
Figure 12B:
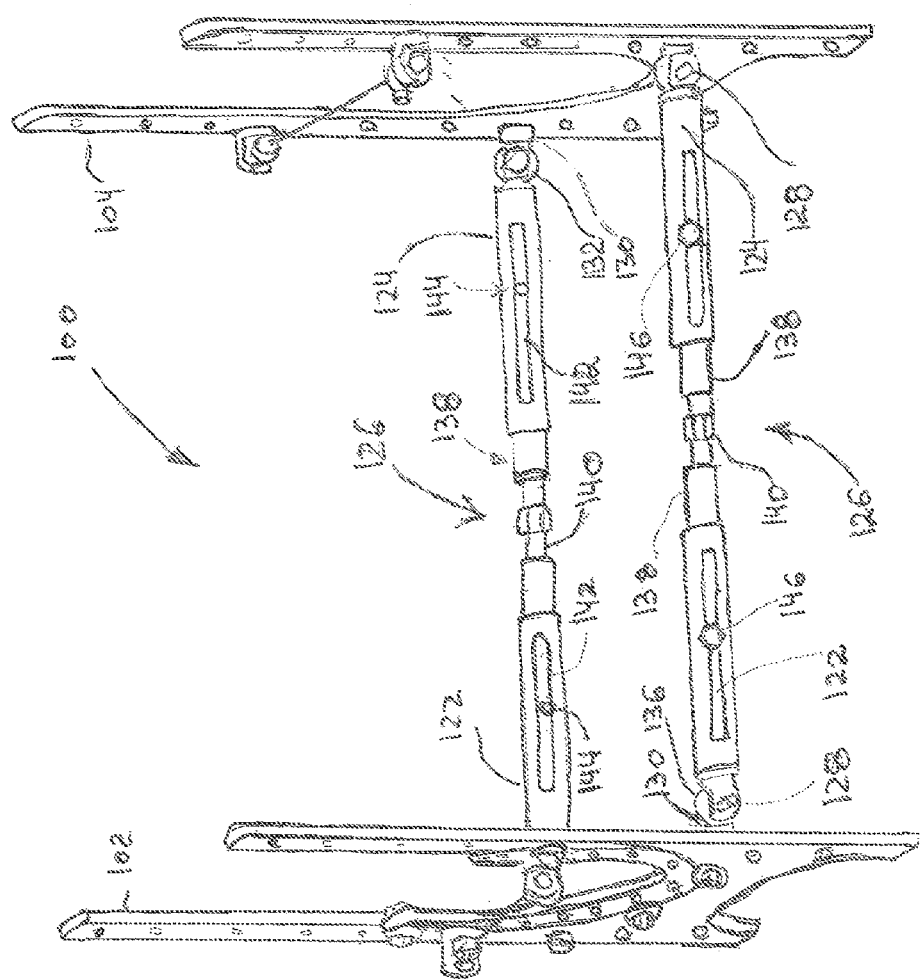

FIGS. 12A-B illustrate perspective views of a collapsible orthopedic fixation assembly 100 in a deployed configuration, according to an exemplary embodiment of the present invention. The assembly 100 includes a first end frame 102, a second end frame 104, and two cross beams 106. A first end 108 of each of the cross beams 106 is connected to the first frame 102 and a second end 110 of each of each of the cross beams 106 is connected to the second frame 104. The cross beams 106 and the connection between the cross beams and the end frames 102, 104 are configured so that relative movement between the end frames and the cross beams can be inhibited when the fixation assembly 100 is in the deployed configuration, thereby providing a stable base for supporting bone-interface components 112.

The end frames 102, 104 include a flat main body having a plurality of mounting holes 114 that can be used for the attachment of the cross beams 106 and for the attachment of support members 116 that are used to support the bone-interface components 112. For example, although the cross beams 106 are shown attached to a pair of the mounting holes 114 that are third from the bottom of the end frames 102, 104, the cross beams 106 can be attached via any other suitable combination of the mounting holes 114. The support members 116 can be mounted using any suitable mounting approach. For example, a support member 116 can include a protruding externally-threaded stud that protrudes through a mounting hole 114 and a removable internally-threaded nut can engage the stud to secure the support member 116 to the respective frame. As another example, a support member 116 can include an internally-threaded hole configured to receive and couple with an externally-threaded fastener that protrudes through a mounting hole 114. In many embodiments, one or more support members 116 are configured so that the support member can be secured to a respective frame member in any angular orientation, thereby allowing the selection of an angular orientation suitable to support a respective bone-interface component in an orientation compatible with the bone-interface component being supported at each end by respective support members 116. To achieve a suitable angular orientation of support members 116 used to support opposite ends of a bone-interface component 112, the bone-interface component 112 can be attached to both of the respective support members 116, the respective support members 116 can be loosely secured to the respective frame via selected mounting holes, and the respective support members 116 can then be fully secured to the respective frame member 102, 104, thereby fixing the orientation of the support members 116 to the frame. In many embodiments, the bone-interfacing components 112 are configured to accommodate different distances between the mounting holes 114 that may be used to support the support members 116 as shown in FIGS. 12A-B.

In many embodiments, the collapsible fixation assembly 100 includes a third frame member 118 that can be attached to of the end frames 102, 104, such as to the first end frame 102 as shown in FIGS. 12A-B. One or both of the end frames 102, 104 can be configured to receive and support a third frame member 118. The third frame member 118 is configured to support at least one bone-interface component 112. The third frame member 118 includes a cylindrical outer surface that is configured to interface with a cylindrical inner surface of the respective end frame 102, 104. The end frames 102, 104 include four mounting holes that are used in conjunction with four fasteners and associated washers 120 to retain the third frame member 118 in the respective end frame 102, 104 in a selected and fixed orientation relative to the end frame.

Each of the cross beams 106 include a first end 122, a second end 124, and a middle portion 126. Each of the first and second ends 122, 124 include an attachment lug 128 configured to attach the cross beam 106 with a respective attachment fitting 130 via a respective attachment fastener 132. The attachment fittings 130 are attached to the respective end frames 102, 104. The attachment fasteners 132 that connect the cross beams 106 to a respective frame are aligned along an axis of rotation 134, about which relative rotation between the cross beams and the respective frame occurs when the fixation assembly 100 is reconfigured from the collapsed configuration to the deployed configuration and vice versa. An interface washer 136 is disposed between the attachment lug 128 and an attachment lug of the attachment fitting 130. The attachment fastener 132 can be used to adjust the amount of compression imposed on the interface washer 136, thereby adjusting the amount of resistance to rotation provided by the connection between the attachment lug 128 and the attachment fitting 130. For example, the attachment lug 128 can have an internally threaded hole configured receive and couple with the attachment fastener 132, the head of which can then be rotated to adjust the amount of compression imposed on the interface washer 136. By adjusting each of the attachment fasteners 132 to a suitable degree, each of the interface washers 136 can be compressed to a degree suitable to provide a suitable level of restraint against relative rotation between the cross beams and the end frames when the fixation assembly 100 is in the deployed configuration.

The cross beams 106 are configured to provide a substantially rigid beam having an adjustable overall length. The middle portion 126 includes end members 138 and an externally-threaded tie rod 140 that engages internally-threaded holes in the end members 138. The tie rod 140 includes an wrenching feature that can be used to rotate the tie rod 140 relative to the end members 138 to, for example, attach the tie rod 140 to the end members 138, and/or to adjust the overall length of the cross beam 106. The end members 138 of the middle portion 126 have cylindrical outer surfaces that slidingly interface with complementary sized cylindrical inner surfaces of the first and second ends 122, 124. Each of the first and second ends 122, 124 includes opposing elongated slots 142 that are positioned and oriented to align with internally-threaded holes 144 in the end members 138. Fasteners 146 are installed in the internally-threaded holes 144 and can be selectively loosened to permit relative translation between an end member 138 a respective end 122, 124, and can be tightened to fix the end member 138 relative to the respective end 122, 124, thereby providing for selective adjustment of the overall length of the cross beam 106. Such adjustability can be used to tailor the overall length of the fixation assembly 100 to a length suitable for the treatment of a specific patient.

While the fixation assembly 100 includes two cross beams 106, any suitable number of cross beams can be used. For example, a single cross beam can be used that provides a suitable level of stiffness between the end frames and is coupled with the end frames so as to allow selective reconfiguration of the fixation assembly between a collapsed configuration in which the end frames are substantially aligned with the single cross beam and a deployed configuration where the end frames are oriented transverse to the single cross beam and in which relative movement between the end frames and the single cross beam can be inhibited. Such a single cross beam can also have an adjustable length. For example, a single cross beam can include the two cross beams 106 of the fixation assembly 100, but with each pair of the first end 122 of the cross beams 106 being structurally connected, and each pair of the second end 124 of the cross beams 106 being structurally connected so as to form a single cross beam assembly having an adjustable overall length.

Figure 13A:
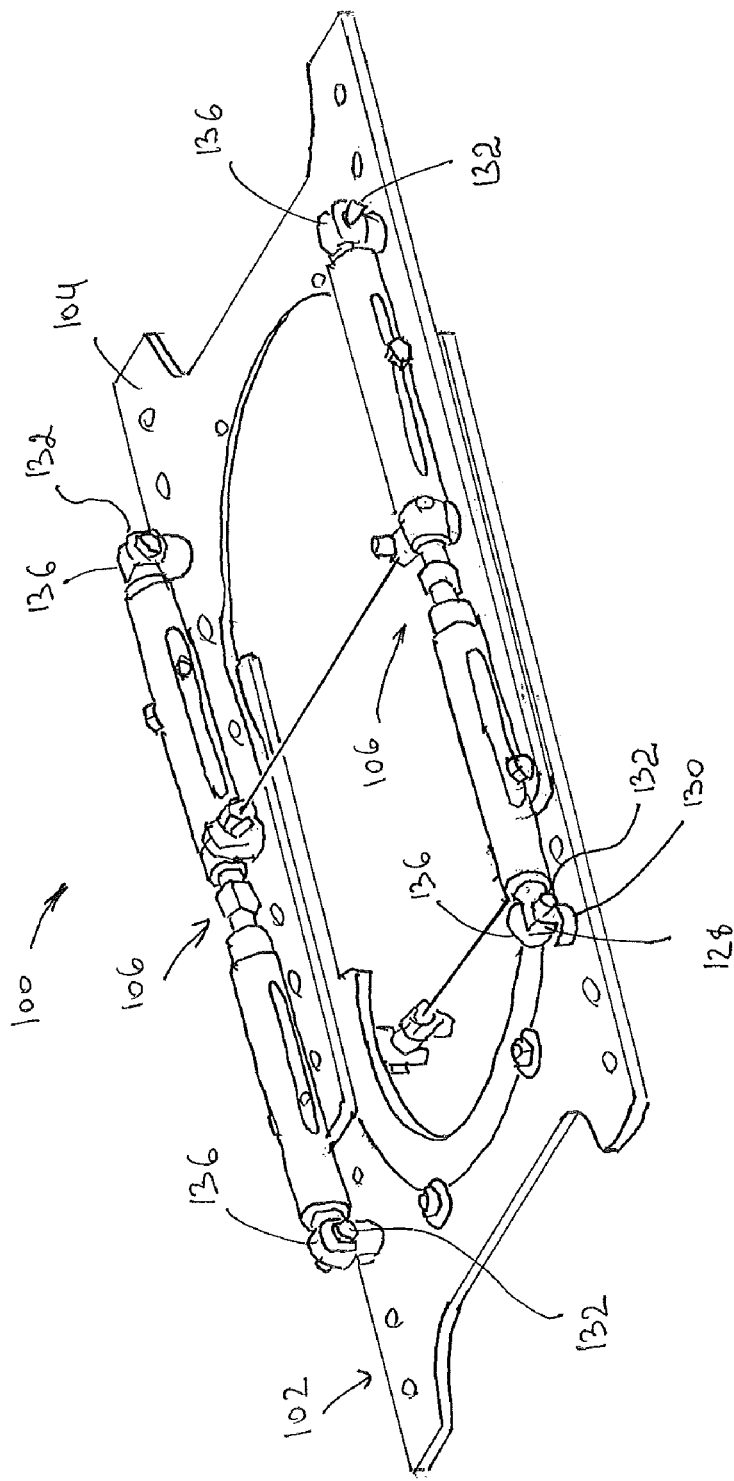
FIGS. 13A-B show perspective views of the collapsible orthopedic fixation assembly of FIGS. 12A-B in a collapsed configuration, in accordance with an exemplary embodiment of the invention.
Figure 13B:
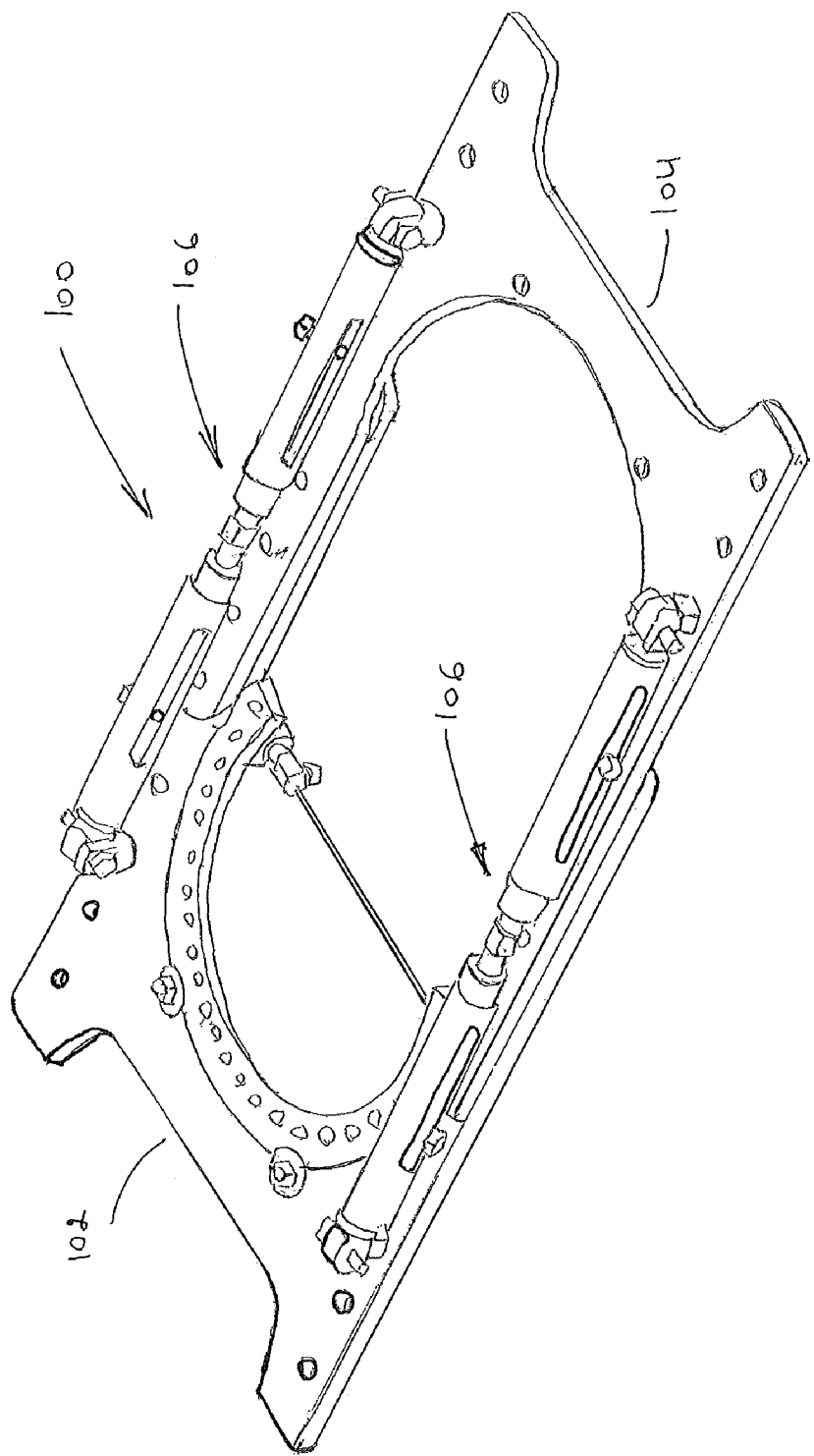

FIGS. 13A-B illustrate a perspective view of the collapsible orthopedic fixation assembly 100 in a collapsed configuration. To reconfigure the fixation assembly 100 from the deployed configuration shown in FIGS. 12A-B to the collapsed configuration shown in FIGS. 13A-B, the attachment fasteners 132 can be loosened to reduce the amount of compression imposed on the interface washers 136, thereby reducing the amount of resistance to rotation provided by the connection between the attachment lugs 128 and the attachment fittings 130. The first and second end frames 102, 104 can then be rotated relative to the cross beams 106 into the collapsed configuration in which the first and second end frames 102, 104 are substantially aligned with the cross beams 106. For example, the collapsed configuration shown in FIGS. 13A-B can be obtained by first rotating the second end frame 104 into substantial alignment with the cross beams 106 and then by rotating the first end frame 102 into substantial alignment with the cross beams, thereby sandwiching the second end frame 104 between the first end frame 102 and the cross beams 106. Optionally, while the fixation assembly 100 is in the collapsed configuration, the attachment fasteners 132 can be tightened to help retain the fixation assembly 100 in the collapsed configuration by inhibiting relative movement between the first and second end frames 102, 104 and the cross beams 106. As an additional optional, the overall length of the cross beams 106 can be adjusted to a minimum, thereby achieving a more compact collapsed configuration for the fixation assembly 100 as compared to when the cross beams 106 are set to an overall length greater than the minimum.

Figure 14:
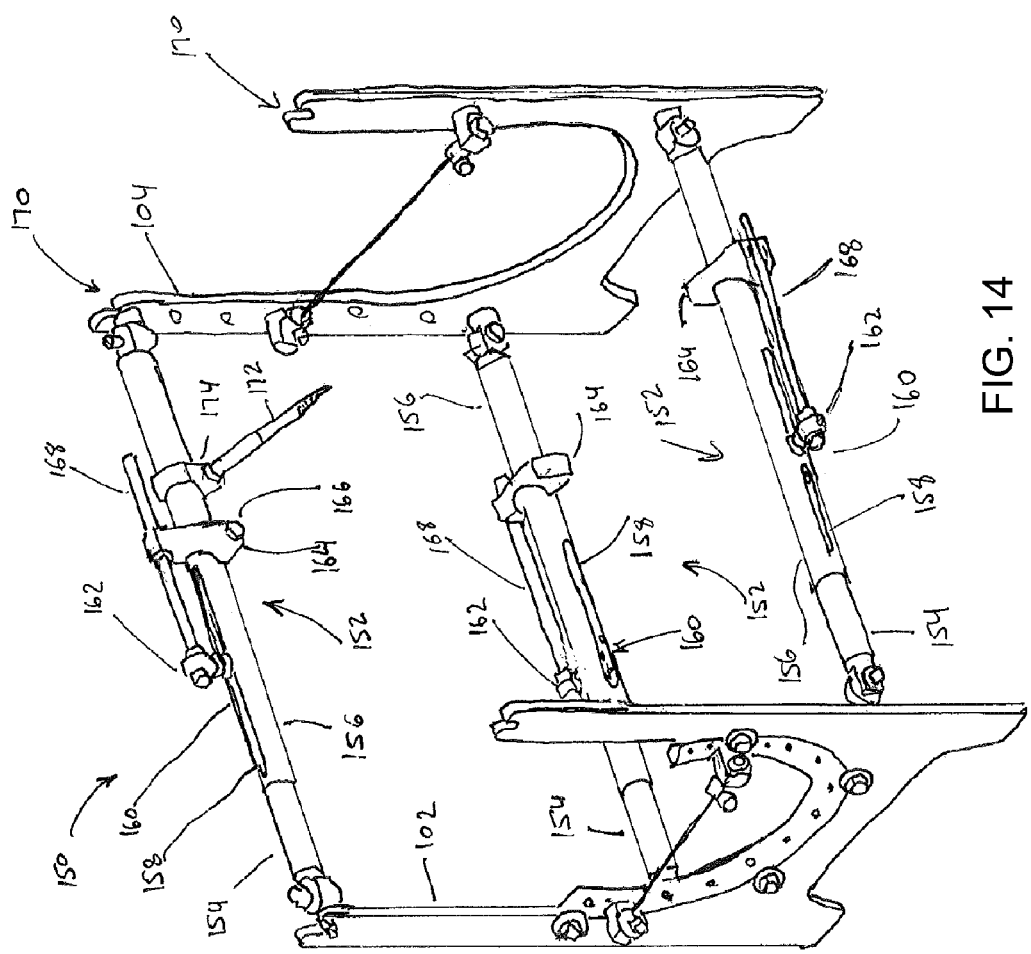
FIG. 14 shows a perspective view of another collapsible orthopedic fixation assembly in a deployed configuration, in accordance with an exemplary embodiment of the invention.

FIG. 14 illustrates a perspective view of another collapsible orthopedic fixation assembly 150 in a deployed configuration, according to an exemplary embodiment of the present invention. The fixation assembly 150 shares common features with the fixation assembly 100 of FIGS. 12A-13B, and therefore applicable portions of the description of the fixation assembly 100 apply to the fixation assembly 150.

The fixation assembly 150 does, however, have some features that differ from the features of the fixation assembly 100. For example, the fixation assembly 150 includes cross beams 152 having end members that directly interface with each other instead of with a middle portion as in the fixation assembly 100. Each of the cross beams 152 includes a first end 154 and a second end 156 that slidingly interfaces with the first end 154. The first end 154 has an external cylindrical surface that interfaces with a complementary sized internal cylindrical surface of the second end 156. The second end 156 includes a pair of opposing elongated slots 158 that are positioned and oriented to align with internally-threaded holes 160 in the first end 154. A fitting 162 is attached to the first end 154 via one of the internally-threaded holes 160 and protrudes from the first end 154 and through a corresponding one of the slots 158. A clamp fitting 164 is secured to the second end 156 via a clamp fastener 166. And a threaded rod and nuts 168 are used to couple the clamp fitting 164 with the protruding fitting 162, thereby setting the overall length of the cross beam 152 by preventing relative translation between the first and second ends 154, 156. The overall length of the cross beams 152 can be adjusted by adjusting the position of the nuts along the threaded rod, thereby setting the distance between the clamp fitting 164 and the protruding fitting 162. And the overall length of the cross beams 152 can also be adjusted by adjusting the position of the clamp fitting 164 along the second end 156.

As shown in FIG. 14, the fixation assembly 150 includes three cross beams, the upper of which is attached to the first and second end frames 102, 104 via attachment slots 170 in the first and second end frames 102, 104. The use of the attachment slots 170 may provide for reduced time to attach one or more additional cross beams to the first and second end frames following reconfiguration of the fixation assembly 150 from a collapsed configuration to a deployed configuration, and for reduced time to detach one or more cross beams from the first and second end frames prior to reconfiguration of the fixation assembly 150 from the deployed configuration to the collapsed configuration.

Attached to the upper most cross beam 152 is a bone-interface component 172, which is attached to the cross beam 152 via a clamp fitting 174. The clamp fitting 174 can suitably positioned along the cross beam 152 and oriented relative to the cross beam 152. Such adjustability of the position and orientation of the clamp fitting 174, coupled with the ability to attach the cross beam 152 to the first and second end frames 102, 104 using different mounting holes, and further coupled with adjustability of the bone-interface component 172 provides the ability to produce a position and an orientation of the bone-interface component 172 to provide a suitable constraint to a bone of a patient. And while the fixation assemblies 100, 150 are shown with specific numbers and locations of cross beams, any suitable number of cross beams can be used in any suitable location. In addition to providing additional support locations for the mounting of bone-interface components, additional cross beams can also be used to provide increased rigidity to the deployed fixation assembly.

Figure 15:
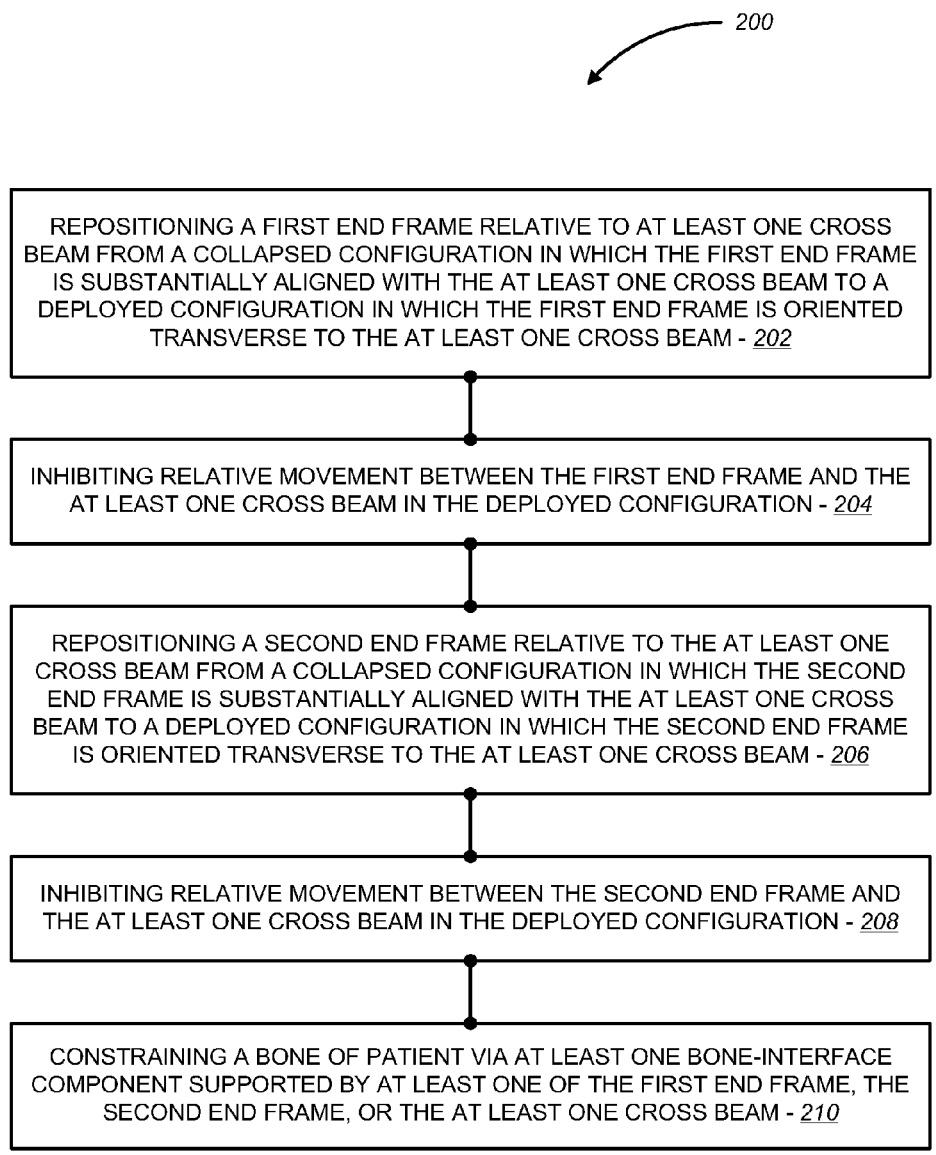
FIG. 15 shows a simplified block diagram illustrating the acts of a method of treating a fracture bone of a patient, in accordance with an exemplary embodiment of the invention.

FIG. 15 illustrates acts of a method 200 of treating a fractured bone of a patient, according to an exemplary embodiment of the present invention. In the method 200, a collapsible fixation assembly, such as the fixation assemblies 100, 150 described herein, is reconfigured from a collapsed configuration to a deployed configuration. While in the deployed configuration, the collapsible fixation assembly is used to constrain a bone of a patient.

The method 200 includes repositioning a first end frame relative to at least one cross beam from a collapsed configuration in which the first end frame is substantially aligned with the at least one cross beam to a deployed configuration where the first end frame is oriented transverse to the at least one cross beam (act 202). Relative movement between the first end frame and the at least one cross beam in the deployed configuration is inhibited (act 204). A second end frame is repositioned relative to the at least one cross beam from the collapsed configuration in which the second end frame is substantially aligned with the at least one cross beam to the deployed configuration in which the second end frame is oriented transverse to the at least one cross beam (act 206). Relative movement between the second end frame and the at least one cross beam in the deployed configuration is inhibited (act 208). And at least one bone of the patient is constrained via at least one bone-interface component supported by at least one of the first end frame, the second end frame, or the at least one cross beam (act 210).

Figure 16:
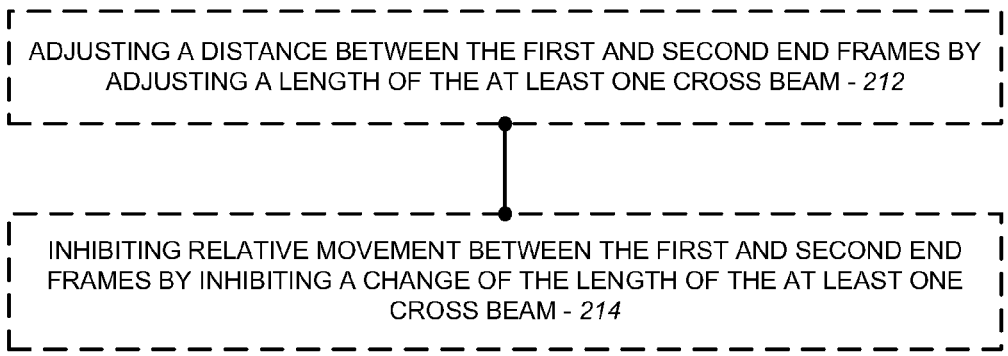
FIG. 16 is a simplified block diagram of acts of a method of treating a fractured bone of a patient, in accordance with an exemplary embodiment of the invention.

FIG. 16 illustrates additional acts that can be used in a method of treating a fractured bone of a patient, in accordance with an exemplary embodiment of the invention. The acts include adjusting a distance between the first and second end frames by adjusting a length of the at least one cross beam (act 212). Relative movement between the first and second end frames can be inhibited by inhibiting a change of length of the at least one cross beam (act 214).

Figure 17:
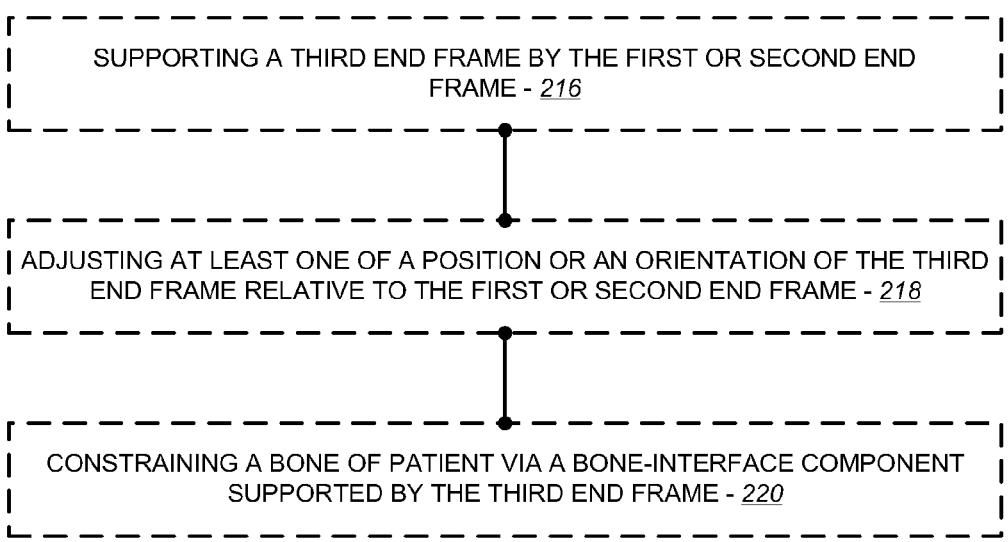
FIG. 17 is a simplified block diagrams of acts that can be used in a method of treating a fractured bone of a patient, in accordance with an exemplary embodiment of the invention.

FIG. 17 illustrates additional acts that can be used in a method of treating a fractured bone of a patient, in accordance with an exemplary embodiment of the invention. The acts include supporting a third end frame by the first or second end frame (act 216). At least one of a position or an orientation of the third end frame can be adjusted relative to the first or second end frame (act 218). And a bone of the patient can be constrained via a bone-interface component supported by the third end frame (act 220).

The method acts described herein can be practiced using any suitably configured fixation assembly. For example, the fixation assemblies 100, 150 described herein can be used to practice the method acts described herein.

The specific dimensions of any of the orthopedic fixation systems, assemblies, and components thereof, of the present invention can be readily varied depending upon the intended application, as will be apparent to those of skill in the art in view of the disclosure herein. Moreover, it is understood that the examples and embodiments described herein are for illustrative purposes only and that various modifications or changes in light thereof may be suggested to persons skilled in the art and are included within the spirit and purview of this application and scope of the appended claims. Numerous different combinations of embodiments described herein are possible, and such combinations are considered part of the present invention. In addition, all features discussed in connection with any one embodiment herein can be readily adapted for use in other embodiments herein. The use of different terms or reference numerals for similar features in different embodiments does not necessarily imply differences other than those which may be expressly set forth. Accordingly, the present invention is intended to be described solely by reference to the appended claims, and not limited to the preferred embodiments disclosed herein.

What is claimed is:

1. A collapsible orthopedic fixation assembly, comprising:
a first cross beam having a first end and a second end opposite to the first end;
a first end frame coupled with the first end of the first cross beam, the first end frame being movable relative to the first cross beam between a collapsed configuration in which the first end frame is substantially aligned with the first cross beam and a deployed configuration in which the first end frame is oriented transverse to the first cross beam and in which relative movement between the first end frame and the first cross beam can be inhibited, the first end frame being configured to support at least one bone-interface component that is configured to constrain a bone of a patient, wherein the first end frame is a flat plate which has an H-shape and comprises a first vertical portion and a second vertical portion having straight and parallel outwardly facing sides running the entire height of the respective first vertical portion and the second vertical portion and a first connecting portion and wherein the first end of the first cross beam is coupled to one of the first vertical portion of the first end frame; and
a second end frame coupled with the second end of the first cross beam, the second end frame being moveable relative to the first cross beam between a collapsed configuration in which the second end frame is substantially aligned with the first cross beam and a deployed configuration in which the second end frame is oriented transverse to the first cross beam and in which relative movement between the second end frame and the first cross beam can be inhibited, the second end frame being configured to support at least one bone-interface component that is configured to constrain a bone of the patient, wherein the second end frame is a flat plate which has the H-shape and comprises a third vertical portion and a fourth vertical portion having straight and parallel outwardly facing sides running the entire height of the respective third vertical portion and fourth vertical portion and a second connecting portion, wherein each of the vertical portions comprises a plurality of mounting holes arranged along the height thereof, said plurality of mounting holes extending entirely through the thickness of each vertical portion and configured to connect to a bone-interface component or a cross beam, wherein the second end of the first cross beam is coupled to the third vertical portion vertical portions of the second end frame, wherein in the collapsed configuration the first vertical portion of the first end frame, the third vertical portion of the second end frame and the first cross beam are positioned parallel and adjacent to one another, wherein in the collapsed configuration the second vertical portion of the first end frame, the fourth vertical portion of the second end frame and a second cross beam coupled to the first and second end frames are positioned parallel and adjacent to one another and wherein the first end frame and the second end frame are collapsible independently of one another.

2. The collapsible orthopedic fixation assembly of claim 1, wherein the first and second ends of the first cross beam are separated by a first distance and the first cross beam is configured for selectable adjustment of the first distance.

3. The collapsible orthopedic fixation assembly of claim 2, wherein the first cross beam comprises a first member having the first end and a second member having the second end, the first cross beam being configured for selectable relative translation between the first and second members.

4. The collapsible orthopedic fixation assembly of claim 3, wherein the first cross beam further comprises at least one adjustable locking mechanism to secure a relative position between the first and second members of the first cross beam.

5. The collapsible orthopedic fixation assembly of claim 4, wherein the first cross beam further comprises a third member configured to couple the first member with the second member, the first cross beam being configured for selectable relative translation between the first and third members and for selectable relative translation between the second and third members.

6. The collapsible orthopedic fixation assembly of claim 1, the second cross beam having a first end and a second end opposite to the first end, the first end of the second cross beam being coupled with the first end frame, and the second end of the second cross beam being coupled with the second end frame.

7. The collapsible orthopedic fixation assembly of claim 6, wherein the first and second ends of the second cross beam are separated by a second distance and the second cross beam is configured for selectable adjustment of the second distance.

8. The collapsible orthopedic fixation assembly of claim 1, further comprising a third cross beam having a first end and a second end opposite to the first end, the first end of the third cross beam being attachable to the first end frame, and the second end of the third cross beam being attachable with the second end frame.

9. The collapsible orthopedic fixation assembly of claim 8, wherein the first and second ends of the third cross beam are separated by a third distance and the third cross beam is configured for selectable adjustment of the third distance.

10. The collapsible orthopedic fixation assembly of claim 1, comprising a support member mountable to at least one of the first end frame or the second end frame to support one of the at least one bone-interface component.

11. The collapsible orthopedic fixation assembly of claim 10, wherein the support member is mounted to one of the first end frame or the second end frame in one of the plurality of mounting holes.

12. The collapsible orthopedic fixation assembly of claim 1, further comprising a third frame member that is mountable to at least one of the first end frame or the second end frame, the third frame member configured to support at least one bone-interface component that is configured to constrain a bone of the patient, at least one of a position or an orientation of the third frame member relative to the respective first or second end frames being adjustable.

13. The collapsible orthopedic fixation assembly of claim 12, wherein:
the third frame member includes a cylindrical outer surface configured to interface with a cylindrical inner surface of at least one of the first and second end members, and
an orientation of the third frame member relative to the respective first or second end frames can be selected and fixed.

14. The collapsible orthopedic fixation assembly of claim 13, wherein the third frame member includes a plurality of holes by which a support member can be mounted to the third frame member.

15. The collapsible orthopedic fixation assembly of claim 1, further comprising a strut-mounted bone-interface component coupled with and supported by the first cross beam.

* * * * *